US009777337B2

(12) United States Patent
Schulze et al.

(10) Patent No.: US 9,777,337 B2
(45) Date of Patent: Oct. 3, 2017

(54) DETECTING ANALYTES

(71) Applicant: ITI Scotland Limited, Glasgow (GB)

(72) Inventors: Holger Schulze, Edinburgh (GB);
Damion Corrigan, Edinburgh (GB);
Till Bachmann, Edinburgh (GB)

(73) Assignee: ITI Scotland Limited, Glasgow (GB)

( * ) Notice: Subject to any disclaimer, the term of this patent is extended or adjusted under 35 U.S.C. 154(b) by 159 days.

(21) Appl. No.: 14/359,284

(22) PCT Filed: Nov. 21, 2012

(86) PCT No.: PCT/EP2012/073240
§ 371 (c)(1),
(2) Date: May 19, 2014

(87) PCT Pub. No.: WO2013/076143
PCT Pub. Date: May 30, 2013

(65) Prior Publication Data
US 2015/0148257 A1 May 28, 2015

(30) Foreign Application Priority Data

Nov. 22, 2011 (GB) .................................. 1120118.3
Jul. 17, 2012 (GB) .................................. 1212662.9

(51) Int. Cl.
C12Q 1/68 (2006.01)
G01N 33/543 (2006.01)
G01N 33/53 (2006.01)
G01N 27/327 (2006.01)
G01N 27/02 (2006.01)

(52) U.S. Cl.
CPC .......... *C12Q 1/689* (2013.01); *C12Q 1/6825* (2013.01); *G01N 27/02* (2013.01); *G01N 27/3277* (2013.01); *G01N 33/5308* (2013.01); *G01N 33/5438* (2013.01); *C12Q 2565/607* (2013.01); *C12Q 2600/158* (2013.01)

(58) Field of Classification Search
None
See application file for complete search history.

(56) References Cited

U.S. PATENT DOCUMENTS

| 6,265,170 B1 | 7/2001 | Picard et al. |
| 2006/0275786 A1 | 12/2006 | Long et al. |
| 2010/0133118 A1 | 6/2010 | Sosnowski et al. |

FOREIGN PATENT DOCUMENTS

| CA | 2371938 A1 | 1/2002 |
| JP | 2002-286736 | 10/2002 |
| JP | 2003-521465 | 7/2003 |
| JP | 2004-177399 | 6/2004 |
| JP | 2005-118049 | 5/2005 |
| JP | 2006520469 A | 9/2006 |
| JP | 2010-520747 | 6/2010 |
| JP | 2011-062210 | 3/2011 |
| JP | 2011-507493 | 3/2011 |
| WO | 2004/081566 A2 | 9/2004 |
| WO | 2005/017202 A2 | 2/2005 |
| WO | 2008-103015 | 8/2008 |
| WO | 2009/072812 | 6/2009 |
| WO | 2009/122159 A2 | 10/2009 |
| WO | 2010060060 A1 | 5/2010 |
| WO | 2011/069997 A2 | 6/2011 |

OTHER PUBLICATIONS

Degefa, Tesfaye Hailu et al., "Electrochemical impedance sensing of DNA at PNA self assembled monolayer", Journal of Electroanalytical Chemistry, 612 (2008), 37-41.
Fang, Bin et al., "Label-free electrochemical detection of DNA using ferrocene-containing cationic polythiophene and PNA probes on nanogold modified electrodes", Biosensors and Bioelectronics, 23 (2008), 1175-1179.
Keighley, Simon D. et al., "Optimization of label-free DNA detection with electrochemical impedance spectroscopy using PNA probes", Biosensors and Bioelectronics, 24, 2008, 906-911.
Liu, Jianyun et al., "In situ hybridization of PNA/DNA studied label-free by electrochemical impedance spectroscopy", Chem. Commun., 2005, 2969-2971.
Macanovic, A. et al., "Impedance-based detection of DNA sequences using a silicon transducer with PNA as the probe layer", Nucleic Acids Research, 2004, vol. 32, No. 2, 1-7.
Park, Jin-Young et al., "Label-Free Impedimetric Sensor for a Ribonucleic Acid Oligomer Specific to Hepatitis C Virus at a Self-Assembled Monolayer-Covered Electrode", Anal. Chem., 2010, 82, 8342-8348.
Raoof, Jahan Bakhsh et al., "Preparation of an electrochemical PNA biosensor for detection of target DNA sequence and single nucleotide mutation on p53 tumor suppressor gene corresponding oligonucleotide", Sensors and Actuators B, 157, 2011, 195-201.

(Continued)

Primary Examiner — James Martinell
(74) Attorney, Agent, or Firm — Gavrilovich, Dodd & Lindsey LLP

(57) ABSTRACT

Provided is a method for detecting analyte in a sample, which method comprises:
(a) contacting the sample with a peptide nucleic acid (PNA) probe;
(b) performing an electrochemical impedance spectrometry (EIS) measurement on the sample;
(c) determining the presence, absence, quantity and/or identity of the analyte from the EIS measurement;
wherein the analyte comprises nucleic acid;
and wherein the quantity of analyte in the sample when the sample is taken is substantially the same as the quantity of analyte in the sample when the sample is subjected to the EIS measurement.

40 Claims, 23 Drawing Sheets

(56) References Cited

OTHER PUBLICATIONS

Kaye, Jeremy, Patents Act 1977: Examination Report under Section 18(3), Application No. GB1212662.9, Oct. 6, 2014.
Mann, Tina L. et al., The application of ultrasound as a rapid method to provide DNA fragments suitable for detection by DNA biosensors, Biosensors and Bioelectronics, 20 (2004), 945-955.
Patel, Manoj K. et al., "Electrochemical DNA sensor for Neisseira meningitidis detection", Biosensors and Bioelectronics, 25 (2010) 2586-2591.
Patolsky, Fernando et al., "Detection of single-base DNA mutations by enzyme-amplified electronic transduction", Nature Biotech., vol. 19, 2001, pp. 253-257.
Prabhakar, Nirmal et al., "Polyaniline Based Nucleic Acid Sensor", J. Phys. Chem., B, 112, 4808-4816, (2008).
Prabhakar, Nirmal et al., "Peptide Nucleic Acid Immobilized Biocompatible Silane Nanocomposite Platform for *Mycobacterium tuberculosis* Detection", Electroanalysis, vol. 22, 2010, pp. 2672-2682.
Liu et al., "Effects of Target Length on the Hybridization Efficiency and Specificity of rRNA-Based Oligonucleotide Microarrays," Applied and Environ. Microbiol., 73(1):73-82, Jan. 2007.
Lazar, Zala, International Search Report, PCT/EP2012/073240, European Patent Office, Feb. 21, 2013.
Search Report, State Intellectual Property Office of China, Application No. 201280066877.X.
Russian Office Action, Application No. 2014125212, Dec. 2, 2015.

A

B

C

DETECTING ANALYTES

CROSS REFERENCE TO RELATED APPLICATIONS

This application is a National Stage Application filed under 35 U.S.C. §371 and claims priority to International Application Serial No. PCT/EP2011/073240, filed Nov. 21, 2012, which application claims priority to Great Britain Application Nos. 1120118.3, filed Nov. 22, 2011 and 1212662.9, filed Jul. 17, 2012, the disclosures of which are incorporated herein by reference.

The present invention relates to methods for detecting an analyte using enhanced electrochemical impedance spectroscopy (EIS) techniques to obtain data on a nucleic acid analyte. The method is advantageous since it can be carried out without the need for amplification of the nucleic acid analyte. This leads to simplification of the procedure and may result in enhanced speed over known assay methods, and therefore may improve time to result (TTR) and facilitate development of such assays in the near patient environment. The present methods are especially advantageous in analyses of wounds and in particular pathogens that are infecting wounds.

Methods for detecting analytes are well known in the field of biochemical analysis. In traditional methods the analyte is labelled, usually with a fluorescent label, which can be detected, for example by fluorescence detection, in order to identify the analyte.

In the past few years in the field of DNA detection, nanoparticles have been used as the labels. These labels will potentially work for any system that permits labelling and involves binding, thus may be useful in a live cell system, as well as proteins and nucleic acids. The nanoparticles have been found to overcome a number of limitations of more traditional fluorescent labels including cost, ease of use, sensitivity and selectivity (Fritzsche W, Taton T A, Nanotechnology 14 (2003) R63-R73 "Metal nanoparticles as labels for heterogeneous, chip-based DNA detection"). Nanoparticles have been used in a number of different DNA detection methods including optical detection, electrical detection, electrochemical detection and gravimetric detection (Fritzsche W, Taton T A, Nanotechnology 14 (2003) R63-R73 "Metal nanoparticles as labels for heterogeneous, chip-based DNA detection"). The use of gold nanoparticles in the detection of DNA hybridization based on electrochemical stripping detection of the colloidal gold tag has been successful (Wang J, Xu D, Kawde A, Poslky R, Analytical Chemistry (2001), 73, 5576-5581 "Metal Nanoparticle-Based Electrochemical Stripping Potentiometric Detection of DNA hybridization"). The use of semiconductor nanocrystals, also called quantum dots, and gold nanoparticles have also been successfully used as fluorescent labels for DNA hybridization studies (West J, Halas N, Annual Review of Biomedical Engineering, 2003, 5: 285-292 "Engineered Nanomaterials for Biophotonics Applications: Improving Sensing, Imaging and Therapeutics").

Despite the advantages discovered by using nanoparticles in DNA detection methods instead of the previous fluorescent labels, there is still a need to improve the sensitivity, selectivity and in particular the speed of the detection methods. Whilst each detection method has a certain degree of sensitivity and selectivity, they each have different limitations and produce different inaccuracies and each is not as quick as desired, especially for near patient environment testing where a short time to result (e.g. approximately 10 minutes) is desirable.

Further to such methods, nanoparticle labelling has been combined with electrophoresis in detecting DNA (see WO 2009/112537). The electrophoresis is employed to speed up binding of the DNA to complementary probes on an electrode surface. The method is advantageous since it may result in enhanced speed and sensitivity over known assay methods.

In addition to this there is also a growing need for cheap and simple detection methods, particularly for DNA in the near patient environment. To reduce cost, simplify methods, and improve speed of detection, it has been known to dispense with labelling altogether. Whilst detection methods that don't use labels might have these advantages, it is challenging to achieve the flexibility and sensitivity of detection that labels provide.

In the past electrochemical impedance spectroscopy (EIS) techniques have been considered for obtaining data on analytes both with and without using labels. The following references provide background details;

Review of applications of EIS to Biosensing—Daniels, J. S., Pourmanda, N., "Label-Free Impedance Biosensors Opportunities and Challenges", Electroanalysis, 19, 2007, 1239-1257.

Review of applications of EIS to Biosensing—Katz, E., Willner, I., "Probing Biomolecular Interactions at Conductive and Semiconductive Surfaces by Impedance Spectroscopy: Routes to Impedimetric Immunosensors, DNA-Sensors, and Enzyme Biosensors", Electroanalysis 15, 2003, 913-947.

Characterisation of impedance spectrum of nanoscale electrodes of various dimensions in KCl solutions—Laureyn, W., Van Gerwen, P., Suls, J., Jacobs, P., Maes, G., Electroanalysis, 13, 2001, 204-211.

AC impedance and spectroscopy for the detection of enzyme activity—Laureyn, W., Van Gerwen, P., Suls, J., Jacobs, P., Maes, G., Electroanalysis, 13, 2001, 204-211.

AC impedance and IDEs in an integrated system—Zou, Z., Kai, J., Rust, M. J., Han, J., Ahn, C. H., "Functionalized nano interdigitated electrodes arrays on polymer with integrated microfluidics for direct bio-affinity sensing using impedimetric measurement." Sens. Acts. A, 136, 2007, 518-526.

"In situ hybridization of PNA/DNA studied label-free by electrochemical impedance spectroscopy", J Liu, S. Tian, P. Nielsen, W. Knoll, Chem. Commun., 2005, 2969-2971.

From this it can be seen that AC impedance measurements (also often called electrochemical impedance spectroscopy, or EIS) typically involve the application of a sinusoidal small amplitude (~10 mV) AC voltage perturbation between two electrodes and the measurement of the resulting current between them as a function of AC frequency, from which the impedance as a function of frequency can be calculated. Changes in such impedance spectra have been shown to provide a method for sensitive label-free measurement of probe-target binding in specific surface films on electrodes, particularly when using interdigitated electrodes (IDE) such as interdigitated microelectrodes (IME) or interdigitated nanoelectrodes (INE). However, these measurements usually rely on equilibration of binding of the analyte either to the electrode, or to a probe attached to the electrode, as this determines the amount of target bound in the layer. The EIS response will thus follow equilibrium thermodynamics. This procedure requires equilibrating for extended periods, often several hours, and sometimes at elevated temperatures, to ensure complete probe-target association prior to measurement. This precludes a rapid time-to-result (TTR).

In addition to this, the impedance response of IDEs has been considered theoretically and analysis is typically carried out using appropriate electrical equivalent circuits, fitting to the response over a wide frequency range to give parameters for equivalent electrical circuit elements (resistors, capacitors, Warburg elements, etc.) from which characteristic physical parameters (e.g. diffusion coefficients, concentrations, layer thicknesses) indicative of changes in electrochemical response can be extracted. Furthermore, sequential measurement at each frequency is usually employed. Together these factors add to the relatively large time-to-results discussed above, because they contribute to extended analysis and measurement times.

Thus, known EIS methods, especially label-free methods, are typically slow, and do not provide satisfactory time to result for use in a near patient environment setting required in the present invention. US 2010/0133118 discloses the use of nucleic acid probes in the detection of nucleic acid using EIS. PNA probes are preferred, but DNA probes may also be used. amplification of the sample is not employed, the signal is instead boosted by concentration of the analyte in the sample. This technique aids in detection sensitivity, but concentration steps are typically long and involve further complex chemistry, meaning that they have the same drawbacks as amplification steps. In particular, they are not suitable for assays in the near patient environment, where time-to-result is very important.

WO 2009/122159 discloses a biosensor for detecting inter alia nucleic acid. It employs PNA probes, typically for detecting mRNA and cDNA. However it also employs an amplification step before analysing using EIS. It therefore suffers from the same drawbacks as the other known methods described here.

In all of the prior art methods described thus far, it is required to increase the amount of nucleic acid in the sample before detection (either by concentration, or amplification), even where more sensitive EIS and label free detection are being employed. However, as has been alluded to, amplification techniques, and the like, require considerable time and extra chemical and physical resource (reaction materials, method steps, apparatus, etc.). Thus nucleic acid detection presents unique problems when speed and sensitivity are important.

It is an aim of this invention to overcome the problems associated with the above prior art. In particular, it is an aim of this invention to provide a method for detecting a nucleic acid analyte with good sensitivity and selectivity which also has improved speed and time to result, and is cheap and simple to carry out.

Accordingly, the present invention provides a method for detecting analyte in a sample, which method comprises:
(a) contacting the sample with a peptide nucleic acid (PNA) probe;
(b) performing an electrochemical impedance spectrometry (EIS) measurement on the sample;
(c) determining the presence, absence, quantity and/or identity of the analyte from the EIS measurement;
wherein the analyte comprises nucleic acid, and wherein the quantity or concentration of analyte in the sample when the sample is taken is substantially the same as the quantity and/or concentration of analyte in the sample when the sample is subjected to the EIS measurement.

In some embodiments, "the quantity or concentration of analyte in the sample when the sample is taken is substantially the same as the quantity and/or concentration of analyte in the sample when the sample is subjected to the EIS measurement" may mean simply that no nucleic acid amplification step has been carried out. Accordingly, the present invention provides a method for detecting analyte in a sample, which method comprises:
(a) contacting the sample with a peptide nucleic acid (PNA) probe;
(b) performing an electrochemical impedance spectrometry (EIS) measurement on the sample;
(c) determining the presence, absence, quantity and/or identity of the analyte from the EIS measurement;
wherein the analyte comprises nucleic acid, and wherein no nucleic acid amplification step has been carried out before the sample is subjected to the EIS measurement.

In another embodiment, the present invention provides a method for detecting an analyte comprising a nucleic acid, in a sample, which method comprises:
(a) subjecting the sample to a sample preparation step to fragment the nucleic acid;
(b) contacting the sample with a peptide nucleic acid (PNA) probe;
(c) performing an electrochemical impedance spectrometry (EIS) measurement on the sample;
(d) determining the presence, absence, quantity and/or identity of the analyte from the EIS measurement.

Typically the sample preparation step comprises heating, sonication, or using a restriction enzyme on the sample to fragment the nucleic acid. Typically heating or sonication are employed to avoid the time, expense and extra reagents that restriction enzymes involve. In preferred embodiments, preparing the sample either by heating or otherwise fragments the nucleic acid such that the average length, or minimum length, of the resulting nucleic acid sequences is 1000 bp or less (bp=base pairs), 900 bp or less, 800 bp or less, 700 bp or less, 600 bp or less, 500 bp or less, 20 bp or more, 30 bp or more, 40 bp or more, 50 bp or more 60 bp or more 70 bp or more, 80 bp or more, 90 bp or more, 100 bp or more, 110 bp or more, 120 bp or more, 130 bp or more, 140 bp or more, or 150 bp or more, from 20-1000 bp, 30-900 bp, 40-800 bp, 50-700 bp, 60-600 bp, 70-600 bp, 80-600 bp, 90-600 bp, 100-600 bp, from 100-500 bp, from 100-400 bp, from, from 100-300 bp, from 110-200 bp, and about 120 bp. In this embodiment, typically the quantity or concentration of analyte in the sample when the sample is taken is substantially the same as the quantity or concentration of analyte in the sample when the sample is subjected to the EIS measurement. This typically means that no nucleic acid amplification step has been carried out.

In this aspect of the invention, the processing carried out in the sample preparation step is not especially limited, provided that it fragments the nucleic acid. Typically this causes the average length, or minimum length, of the nucleic acid sequences to lie within the preferred ranges discussed above. Typically, but not exclusively, the processing is a heating step to cause fragmentation of the nucleic acid. This is particularly preferred if the sample comprises large nucleic acids such as genomic DNA (gDNA) or ribosomal RNA (rRNA). Typically, heating such large nucleic acids causes fragmentation to occur into sequences of 1000 bp or less. Regular PCR typically involves heating to denature the nucleic acid (convert double stranded to single stranded nucleic acid so as to allow replication), but it aims to avoid fragmentation so as to prevent degradation of the DNA sample. This is confirmed in the article "Effect of heat denaturation of target DNA on the PCR amplification", Gene., 1993, 123(2), pp 241-4, where Gustafson et al. state:

We have shown that lengthy denaturation times of template DNA ranging from 1 to 7 min at pH 7.0-8.0, that are often employed prior to the start of a PCR reaction, result in marked degradation of the template. This can result in a significant reduction in the yield of PCR products larger than 500 bp, by up to 99% . . . . This decrease in product yield is likely due to the increased degradation of the template or target DNA as a result of pre-amplification denaturation (PAD). We therefore recommend that when amplifying larger pieces of DNA, the template DNA should not be exposed to PAD prior to a PCR reaction, irrespective of the starting pH of the template solution.

Therefore, when dealing with large nucleic acids, such as genomic DNA or the like, treatments which can cause fragmentation (such as heat treatment) have been avoided, since they are severely disadvantageous. The present inventors have, however, surprisingly found that fragmentation is desirable in the present method: instead of interfering detrimentally with the results of the analysis, the inventors have found that fragmentation may improve the EIS signal, and is therefore helpful in avoiding the need for amplification of the analyte, such as by PCR, altogether.

The length of time of heating, and the temperature employed will depend on the nature of the sample under investigation, and also on the chemical nature of the surrounding medium (the pH, the presence of buffers, salts, catalysts, etc.). It is not especially limited provided that appropriate fragmentation is achieved. Typically a time of from 10 s to 1 hr will be employed, preferably from 30 s to 30 minutes, from 1 minute to 20 minutes, from 2 minutes to 15 minutes and from 3 minutes to 10 minutes. Typically about 5 minutes is preferred. The temperature will typically be from 60-100° C., from 70-99° C., from 80-99° C., from 90-99° C. and typically about 95° C.

From FIG. 20 it can be seen that denaturation of the genomic DNA for 5 mins at 95° C. in 2×SSC coincided with an increase in DNA fragmentation and an increase in the impedimetric signal. The role of DNA fragmentation has been assessed for glass microarrays with long hybridisation times but has hitherto not been investigated for the binding of genomic DNA for impedimetric detection. As has been highlighted above, it is known that incubation of DNA at a high temperature such at 95° C. causes fragmentation of long strands of DNA and reduces PCR efficiency. Thermal DNA fragmentation has been shown to produce strands of less than 800 bp. Without being bound by theory, the most likely explanation for the observation that EIS signal was greatest following incubation of DNA for 5 mins at 95° C. was that the shorter fragments were better able to access and bind with the probe sequence which resided in close proximity to the electrode surface. For EIS based sensing of nucleic acid hybridisation there will be a trade-off between fragment size and signal increase. Longer fragments should induce greater signal increases because of their increased electrostatic effect on the redox probe in solution, and by greater blocking of tunnelling currents through the sensing layer; however, hybridisation efficiency for long fragments will be reduced owing to steric hindrance effects at the electrode surface and the possible formation of secondary structures. In the Examples presented herein, the data on target fragmentation time show that this relationship between probe length, fragment length and EIS signal exists. The fragmentation data suggests target strand lengths of approximately 120 bp in length are responsible for EIS signal increases, and thus may aid in the ability to detect nucleic acid without amplification. In contrast to this, much of the literature on EIS based nucleic acid detection reports results obtained with short (20 bp) artificial oligonucleotides.

In the context of the present invention, the sample is in some embodiments typically subjected to EIS without increasing the quantity or concentration of the analyte in the sample, such as by avoiding amplification or avoiding combining multiple samples in a manner so as to concentrate the analyte, or avoiding concentrating the sample e.g. by removing liquid medium. Thus, the quantity and/or concentration of analyte in the sample when the sample is taken is substantially the same as the quantity and/or concentration of analyte in the sample when the sample is subjected to the EIS step. In this case, the quantity or concentration need not be absolutely identical, and indeed this is not always possible since standard sample preparation techniques may sometimes change the quantity or concentration to a small degree. Thus substantially the same means the same to the extent that this is possible allowing for standard sample preparation techniques for assaying for nucleic acid. Such standard sample preparation techniques may involve lysing cells, cleaning up the sample and the like. Some purification is also allowable, provided that this does not lead to concentration or amplification (for example, if species that might interfere with the assay are removed from the sample). In some embodiments, the sample may be introduced to the PNA probe in crude form with little or no sample preparation.

Thus, in some embodiments the invention uses no amplification step and no concentration step prior to EIS measurement. Accordingly, in these embodiments it employs no PCR step or RTPCR step, unlike prior art methods.

The analyte is not especially limited, provided that it is a nucleic acid. Any nucleic acid may be analysed, but in typical embodiments, the nucleic acid analyte comprises a large nucleic acid, such as ribosomal RNA and/or genomic DNA (rRNA and gDNA). It is particularly preferred that the analyte is of a type that provides a strong EIS signal. Thus, in some embodiments the analyte nucleic acid comprises 1000 bases (1 kb) or more, more preferably 10 kb or more, 100 kb or more, 1 Mb or more and 5 Mb or more. As has been mentioned, typically genomic DNA may be fragmented or cut into smaller sections to aid in processing: thus the gDNA analyte may be 1 Mb or more, 2 Mb or more, 3 Mb or more, 4 Mb or more, or 5 Mb or more in size in some embodiments. Ribosomal RNA may be smaller in size compared with genomic DNA, due to its presence in a larger number of copies, which will give a better EIS signal. Typically the rRNA analyte may be 1.0 kb or more, 1.1 kb or more, 1.2 kb or more, 1.3 kb or more, 1.4 kb or more and 1.5 kb or more. Alternatively, the rRNA analyte may be 1.6 kb or more, 1.7 kb or more, 1.8 kb or more, 1.9 kb or more, 2.0 kb or more or 2.5 kb or more. Further alternatively the rRNA analyte may be 3.0 kb or more, 3.5 kb or more, 4.0 kb or more, or 4.5 kb or more. As has been mentioned, it is further preferred that this sample is processed such that the average length of the nucleic acid sequences is 20 bp or more, 30 bp or more, 40 bp or more, 50 bp or more 60 bp or more 70 bp or more, 80 bp or more, 90 bp or more, 100 bp or more, 110 bp or more, 120 bp or more, 130 bp or more, 140 bp or more, or 150 bp or more. Typically, after processing the average length of the nucleic acid sequences will be 1000 bp or less, 900 bp or less, 800 bp or less, 700 bp or less, 600 bp or less, or 500 bp or less, such that preferred lengths are from 30-1000 bp, 40-900 bp, 50-800 bp, 55-600 bp, 60-500 bp, 70-400 bp, 80-300 bp, 90-200 bp, 90-180 bp, 90-150 bp, 100-140 bp, 110-130 bp, and about 120 bp.

The PNA probe is not especially limited, provided that it is suitable for detecting the analyte of interest. PNA probes are desirable due to their ability to improve the sensitivity of detection in EIS (see FIG. 9 and FIG. 10). Suitable PNA probes are selected such that they will bind to the target analyte.

Typically, but not exclusively, the PNA probe further comprises a spacer, such that the probe comprises a spacer portion and a PNA portion. The spacer portion is intended to preferentially attach to the electrode surface in order to raise the PNA portion of the probe away from the surface of the electrode. This may improve the hybridisation efficiency of the PNA probe.

The nature of the spacer is not especially limited, provided that it does not interfere detrimentally with the hybridisation efficiency of the PNA. However, in some embodiments, the spacer may comprise an organic molecule comprising one or more of the following groups: a terminal group capable of attaching to a surface—preferably a terminal amine group (which may be a primary, secondary or tertiary amine group), a terminal hydroxy group, or a terminal thiol group; an alkane group; an alkene group; an alkyne group; an ether group; and/or a carbonyl group. The number of atoms in the backbone of the spacer group (the atoms situated directly between the electrode and the PNA portion) is not especially limited, provided that sufficient space is given to improve hybridisation efficiency. In typical embodiments, there may be 3 or more atoms in the backbone, 4 or more, 5 or more, 6 or more, 7 or more, 8 or more, 9 or more, 10 or more, 11 or more, or 12 or more. More typically, there may be from 5-30 atoms, or from 6-25 atoms, or from 7-24 atoms, or from 8-23 atoms in the backbone. More typically the number of atoms in the backbone may be from 9-23, from 10-23, from 3-18, from 5-15, from 5-13 and from 5-10 atoms.

Examples of preferred spacers include compounds having the following formulae:

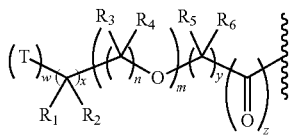

where T is a terminal group capable of attaching to a surface; $R_1$, $R_2$, $R_3$, $R_4$, $R_5$ and $R_6$ are each independently organic groups; w is an integer of 0 or 1; x is an integer of from 0-15; y is an integer of from 0-15; z is an integer of 0 or 1; n is an integer of from 0-10; m is an integer of from 0-15; and wherein [n·m+w+x+y+z] is an integer of at least 3. In the formula, the number of atoms in the backbone of the spacer is determined by w, x, y, z, n and m and is simply [n·m+w+x+y+z].

T is not especially limited, provided that it is a group capable of attaching the spacer portion of the probe to a surface, such as an electrode surface. However, typically T is selected from the following groups: —$NH_2$, —$NHR_7$, —$NR_7R_5$, —SH, —$SR_9$, —OH, —$OR_{10}$.

In some embodiments, the spacers may have the following formula in which x from the above formula is 0:

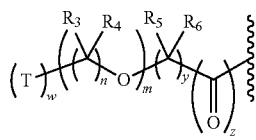

wherein all of the variables have the same meaning as already defined above.

Typically, the spacers may be any compound of any one of the following formulae:

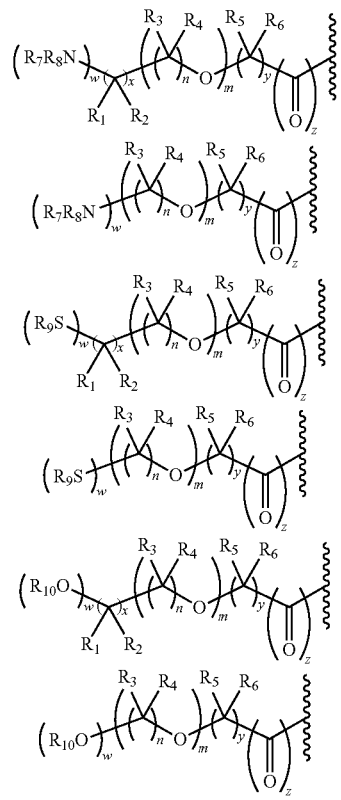

wherein all of the variables have the same meanings as defined above, and wherein $R_7$, $R_5$, $R_9$ and $R_{10}$ are each independently organic groups.

As has been mentioned, $R_1$, $R_2$, $R_3$, $R_4$, $R_5$, $R_6$ $R_7$, $R_8$, $R_9$ and $R_{10}$ are each independently organic groups. In all of the embodiments mentioned in connection with this invention, both above and in the following, the organic groups are not especially limited and may be any functional group or any atom, especially any functional group or atom common in organic chemistry, including an H atom. Thus, organic group may have any of the following meanings. The organic group may comprise one or more atoms from any of groups IIIA, WA, VA, VIA or VIIA of the Periodic Table, such as a B, Si, N, P, O, or S atom (e.g. OH, OR, $NH_2$, NHR, $NR_2$, SH, SR, $SO_3H$, $PO_4H_2$ etc.) or a halogen atom (e.g. F, Cl, Br or I) where R is a lower hydrocarbon (1-6 C atoms) or a higher hydrocarbon (7 C atoms or more, e.g. 7-40 C atoms).

The organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1 40 C atoms. The hydrocarbon group may thus be a lower hydrocarbon (1-6 C atoms) or a higher hydrocarbon (7 C atoms or more, e.g. 7-40 C atoms). The lower hydrocarbon group may be a methyl, ethyl, propyl, butyl, pentyl or hexyl group or regioisomers of these, such as isopropyl, isobutyl, tert-butyl, etc. The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the organic group may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The organic group may also comprise derivatives of these groups, such as carboxylic acid anhydrydes and carboxylic acid halides.

In addition, any organic group may comprise a combination of two or more of the organic groups and/or functional groups defined above.

In some embodiments all of $R_1$, $R_2$, $R_3$, $R_4$, $R_5$, $R_6$ $R_7$, $R_8$, $R_9$ and $R_{10}$ are lower alkyl groups, and most typically they are all H atoms.

Typically x+y is greater than or equal to 1. Typically w is 1. Typically z is 1. Most typically both of w and z are 1.

Typically the multiple of n and m is controlled (as part of controlling the value of [n·m+w+x+y+z]) to achieve the preferred number of atoms in the backbone such that the number is as mentioned above. Typically n is an integer of from 1-3 and most typically n is 2. In some embodiments, m is an integer of from 1 to 5, and most typically m is 2 or 3.

Some more typical spacers are selected from compounds of the following formulae, where w=1, n=2, y=1, z=1 and preferably, x=0:

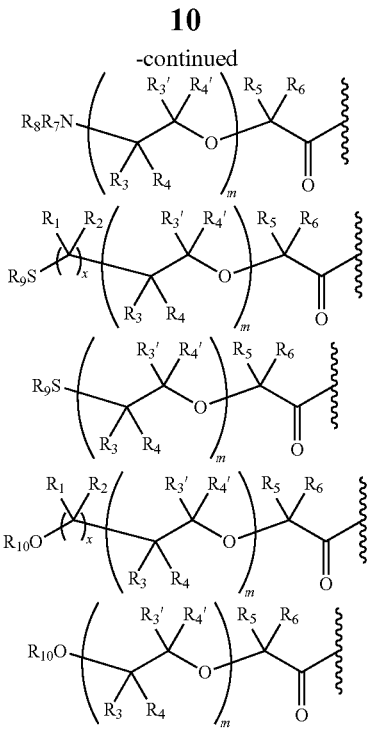

where the variables have the same meanings as already defined above; m is an integer of from 1-7, from 1-6, from 1-5, from 1-4 or from 1-3, such as where m is 1, 2, 3, 4, 5, 6 or 7; x is an integer of from 1-15, from 1-13, from 3-15, from 3-13, from 3-11, from 5-15, from 5-13 or from 5-11; $R_3$ and $R_3'$ may be the same or different and $R_4$ and $R_4'$ may be the same or different. Preferably $R_3$ and $R_3'$ are the same and $R_4$ and $R_4'$ are the same. More preferably all of $R_3$, $R_3'$, $R_4$ and $R_4'$ are the same. Typically all of $R_3$, $R_3'$, $R_4$ and $R_4'$ are H.

In most embodiments, all of $R_1$ to $R_{10}$ are lower alkyl groups or H, and in the most typical embodiments all of $R_1$ to $R_{10}$ are H atoms. Some of the most preferred spacers have the following formulae:

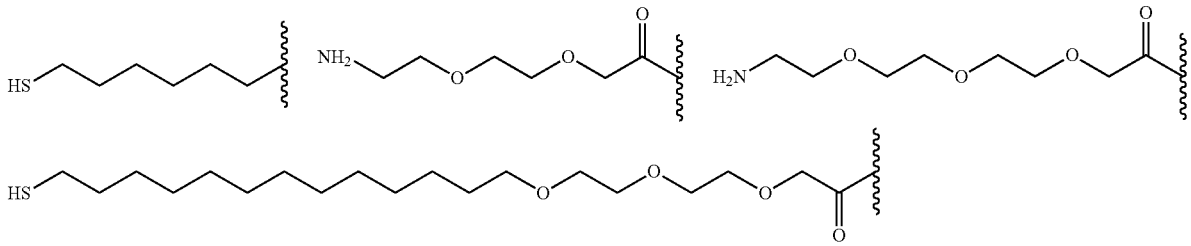

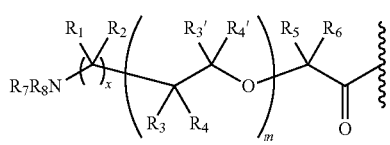

having 7, 9, 12 and 23 atoms in the backbone respectively.

In all of the above formulae, the wavy line represents the bond attachment from the spacer to the PNA. Typically the spacer attaches to the electrode surface through the terminal group.

The EIS method is not especially limited, provided that it is sufficient to determine the presence, absence, identity and/or quantity of the analyte. However, preferably the EIS step comprises the following sub-steps:

i) applying an alternating voltage to the analyte, wherein the alternating voltage comprises a plurality of superimposed frequencies sufficient to distinguish the presence of the analyte by electrochemical impedance spectrometry (EIS); and ii) determining the presence, absence, identity and/or quantity of the analyte from EIS data.

This aspect of the invention preferably utilises statistical analysis to determine a set of frequencies to be superposed and applied in step (i). Statistical methods for determining frequencies in this manner are well known in the art, and the skilled person may employ any known method to determine the set of frequencies to use in the present methods. Such methods can, for example, be found in "Statistical methods in Experimental physics" (2nd Edition) by World Scientific Publications Co. Pte. Ltd. Singapore. Ed. By F. James (2006) ISBN 981-256795.

Other methods of determining the set of frequencies may be employed if desired. For example, for a particular system (e.g. specific electrode/solution/analyte combination) an empirical method may be employed in advance to find a set of frequencies that will suffice as a standard for that particular system. The standard may then be employed in that system without calculating the required frequencies on every occasion the method is performed. Any other method may also be employed, either in real time or in advance, provided that it produces a viable set of frequencies to employ and does not adversely affect TTR.

No matter which method is used to determine the set of frequencies, the set should include at least the minimum number of frequencies required to be sufficient to distinguish the presence of the analyte using EIS. Additional frequencies to the minimum may of course be employed, if desired.

The method may in some embodiments, either in addition to the set of frequencies or in place of the set of frequencies, involve determination of other parameter(s) that in themselves will define a set of frequencies, and thus aid in achieving detection of the presence and/or quantity of the analyte. In each case, the frequencies and/or parameters are selected with a view to providing the fastest time to result through data analysis.

Typically the set of frequencies and/or parameters is sufficient to distinguish the presence or absence of the analyte. The specification of the set of frequencies is not particularly limited, and they may be defined as a set of specific individual frequencies, a set of frequencies within a range, and/or a single frequency with spacings from it, which define further frequencies in the set.

The analysis of the results of the EIS measurements using the superposed frequencies is preferably statistical and does not need to employ an equivalent circuit method of analysis, which typically enables faster discrimination. However, the equivalent circuit method, and any other method, is not precluded provided that TTR is not adversely affected. Fast Fourier transform (FFT) analysis may be used to extract the necessary EIS data, and this information is employed to provide analyte information. Such FFT techniques are well known in the art, and the skilled person may employ any such technique in the present invention, as desired. As mentioned above, preferably information on the analyte presence or absence may be obtained from the EIS data, and more preferably the quantity of the analyte present may also be determined.

The invention confirms that EIS biosensing and discrimination can be achieved using a small number of points over a restricted range of frequency (in Example 1 (see below) seven points over one decade of frequency), which enables the simultaneous application of a multiwaveform (in Example 1, a multisine) EIS perturbation containing the necessary frequencies, with fast Fourier transform (FFT) analysis used to extract the necessary information. Such a procedure enables measurement and analysis using commercially available instrumentation within a few seconds, enabling EIS measurement on a realistic timescale for rapid and robust detection.

Any nucleic acid analyte may be detected in the present invention, and the method of detection will depend on the type of analyte involved. The set of frequencies employed in the invention will depend on the type of binding occurring for each particular system under investigation, as well as the physical nature of the system itself (electrode type, electrode composition, electrode dimensions, analyte composition, solvent/liquid medium type, electrolyte etc.). For similar systems, standard frequency sets may be employed, and for new systems or analytes a real-time statistical calculation may be employed, as explained above.

As has been mentioned, the EIS step is not especially limited. Thus, alternatively the EIS step may comprise the following sub-steps:

i) applying an alternating voltage to the analyte;
ii) determining the rate of change of EIS measurements across the analyte;
iii) determining the presence, absence, identity and/or quantity of the analyte from rate of change data.

It is particularly preferred in this aspect of the invention that the EIS measurements are measurements of electron transfer resistance, Ret. For typical EIS measurements made in real time, one parameter particularly sensitive to probe film formation and probe target hybridisation is the electron transfer resistance, Ret, of a redox couple present in the system (e.g. $[Fe(CN)_6]^{3-/4-}$). This parameter is well known in the art, and may be calculated from the width of the semicircular feature in a Nyquist plot of the EIS spectra.

This aspect of the invention provides an IDE measurement protocol to enable in situ kinetic measurement of the EIS response for analyte binding, either with the electrode surface or via probe-analyte hybridisation. In common with the employment of multiple superposed frequencies, it leads to much shorter EIS measurement time. Also in common with the first aspect, any analyte may be detected, and the specifics of the method of detection will depend on the type of analyte involved. Some analytes may bind to the electrode directly, whilst others may bind to a probe or complementary molecule on the surface of the electrode. The exact nature of the Ret data will depend on the type of binding envisaged for each particular system under investigation.

As has been alluded to above, in this aspect of the invention, it is preferred that both oxidation states of the redox probe (e.g. ferricyanide and ferrocyanide) are present in the solution. This ensures the DC potential at the IDEs is fixed by the reduction potential of redox probes throughout the method and means that potentials can be applied between the two IDEs without using an external reference electrode. This enables the ready application of a small amplitude EIS perturbation voltage between the two electrodes in the IDEs to measure the EIS response. Such measurements enable the EIS response to be measured with time on exposure to the solution.

As has been mentioned, the currently known EIS protocol measures the approach to equilibrium of electrode/analyte binding (or analyte/probe binding as in the case where a probe is attached to the electrode). This results in a change (typically increase) in the EIS signal to a constant value, indicative of equilibration. In this case, as the measurement is taken in the solution, the time for equilibration and equilibrium EIS signal are determined in real time, leading to optimum equilibrium measurement. However, the time to result is slow, since complete equilibration is required before a result can be determined, and this is often a lengthy process, controlled by the rates of analyte binding and release. In this aspect of this invention, as described above, the rate of increase of the EIS signal is used and analysed to determine the concentration of analyte in solution; as electrode/analyte binding (or probe/analyte binding) is measured kinetically. This can be achieved with a much more rapid TTR, of minutes or less, and full equilibrium does not need to be reached.

In the present invention, the EIS data preferably comprises data parameters derived from the complex impedance (x+iy). These parameters are well known to the person skilled in the art and may be selected from one or more of the following:

Real component (x)
Imaginary component (y)
Modulus or absolute value $[r=|z|=(x^2+y^2)^{1/2}]$
Angle $[\theta=\tan-1(y/x)]$
Principal component 1
Principal component 2

The number of superimposed frequencies employed in the invention is not especially limited, provided that they are suitable for analysis using EIS to give the identity and/or quantity of the analyte to the required accuracy. Typically, the minimum number of superimposed frequencies is from 2-20. More preferably the minimum number of superimposed frequencies is at least 3-10, i.e. at least 3, at least 4, at least 5, at least 6, at least 7, at least 8, at least 9 or at least 10. Most preferably the number of superimposed frequencies is about 7.

As has been mentioned, it is preferred that the present method takes place in a liquid medium. Preferably the liquid medium is selected so as to aid in the process. The medium is not especially limited provided that the method is not impaired, and acid or basic media may be employed.

The present invention will be described in further detail with reference to the accompanying Figures, in which.

Figure 3:
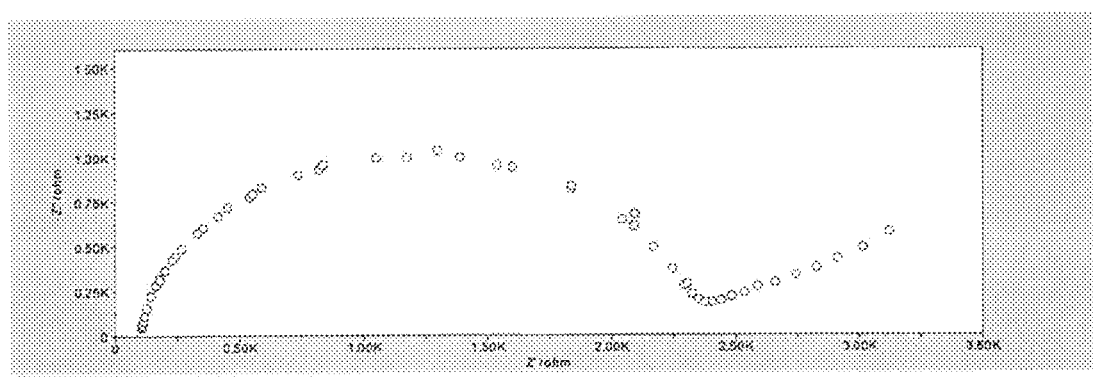

FIG. 3 shows the EIS response of gold protein macro-electrodes (6700 pM antibody) from normal single sine sequential EIS measurement with approximately 23 seconds simultaneous FFT analysis (black—recording time over two minutes; red—5 multisine EIS measurement over 9 seconds; blue—15 multisine EIS measurement every 9 seconds).

Figure 4:
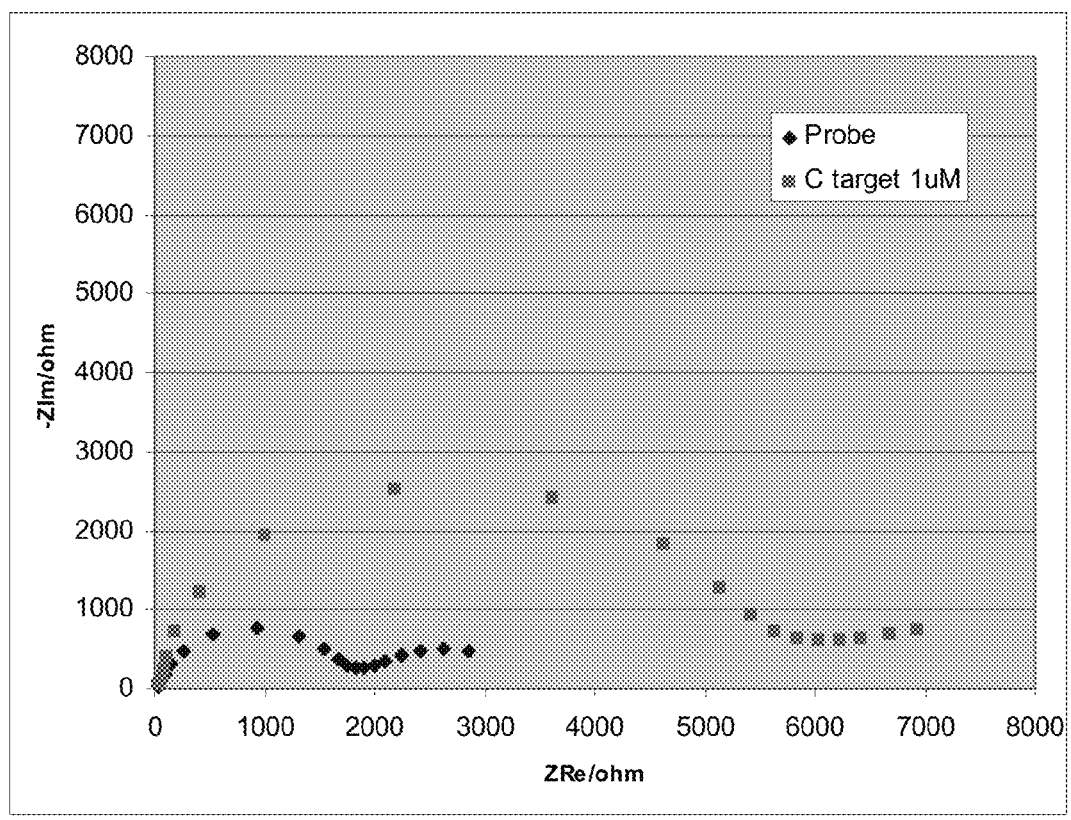

FIG. 4 shows a comparison of the Nyquist plots of modified gold electrode with 69 mer HCV DNA probe and blocked with 1 mM MCH (diamonds), and hybridization with 1 µM of complementary target (ITI 025) (squares). The impedance measurements were carried out in 2×SSC containing 10 mM $[Fe(CN)_6]^{3-}$ and 10 mM $[Fe(CN)_6]^{4-}$ (plus probe or target) at an applied dc potential between the electrodes in the IDE pair of 0 V.

Figure 5:
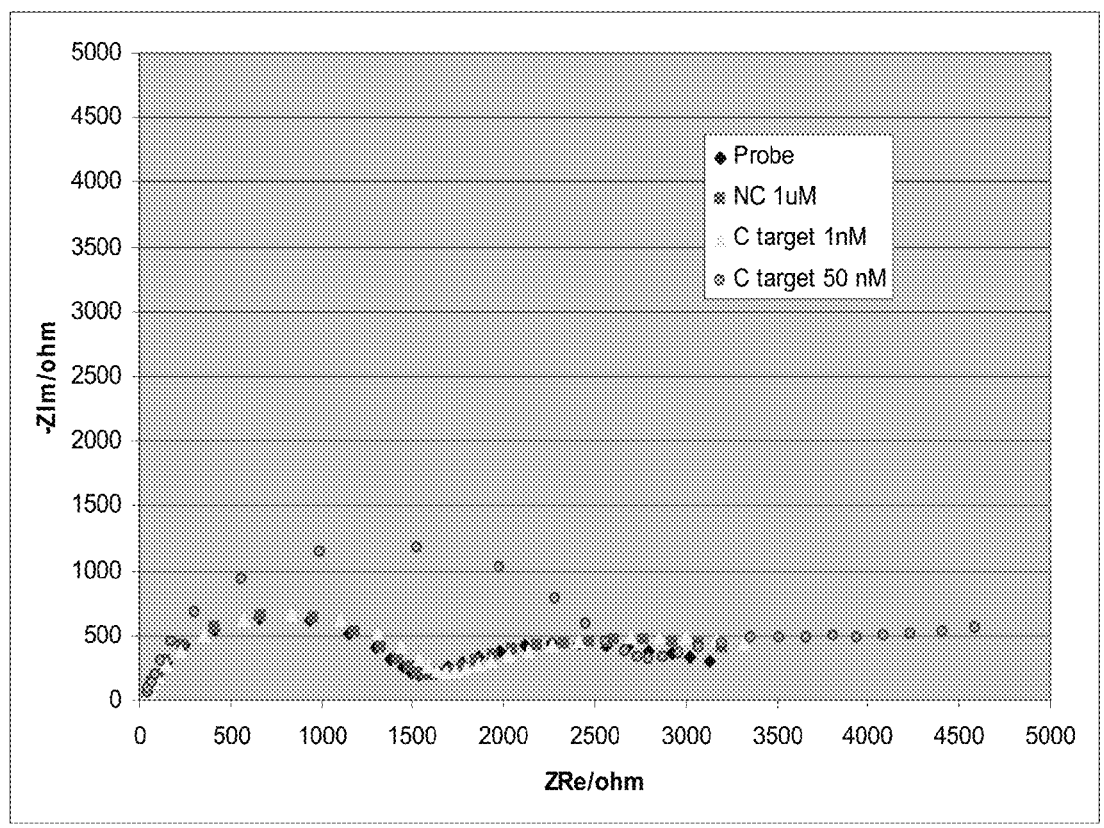

FIG. 5 shows a comparison of the Nyquist plots of modified gold electrode with 69 mer HCV DNA probe and blocked with 1 mM MCH (diamonds), hybridization with 1 µM of non-complementary target (ITI 012) (squares), hybridization with 1 nM (triangles) and 50 nM (circles) complementary target (ITI 025). The impedance measurements were done in 2×SSC containing 10 mM $[Fe(CN)_6]^{3-}$ and 10 mM $[Fe(CN)_6]^{4-}$ (plus probe or target) at an applied DC potential between the electrodes in the IDE pair of 0 V.

Figure 6:
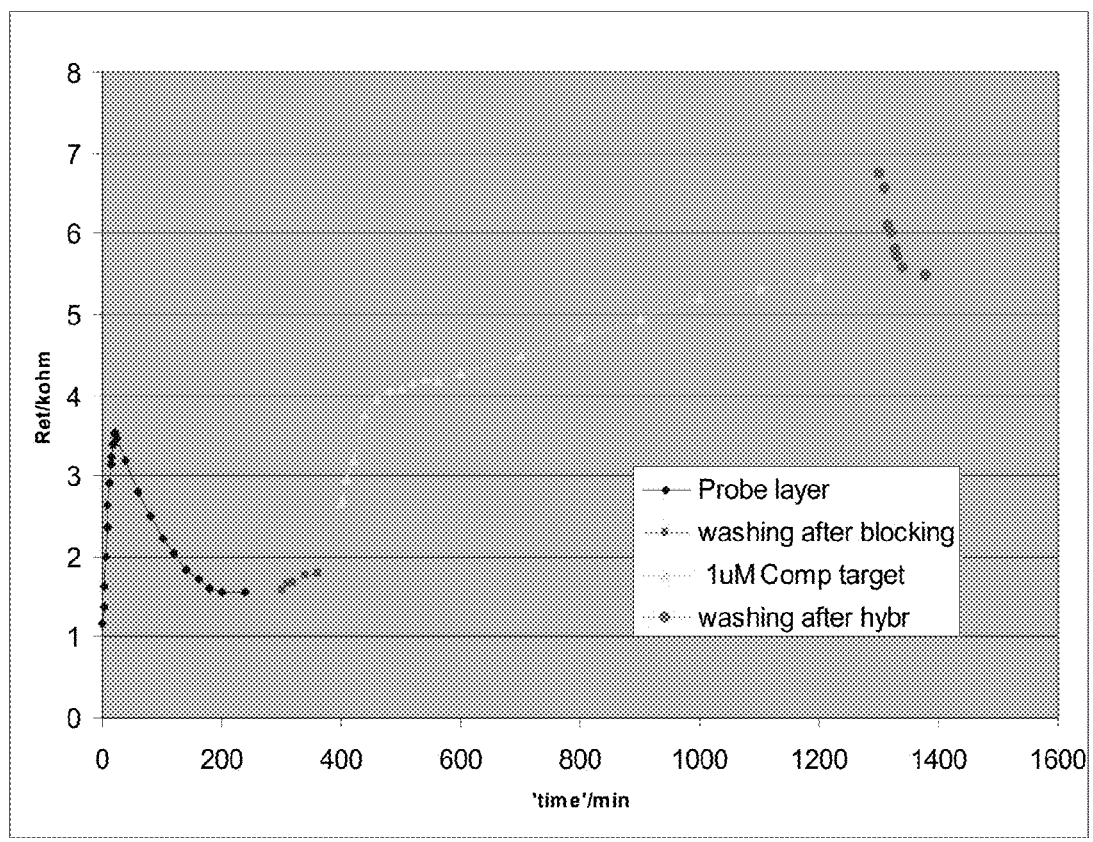

FIG. 6 shows Ret versus time EIS measurements during probe (thiol-DNA) layer formation (diamonds), after blocking with MCH (squares), during hybridization with 1 µM complementary target (triangles) and washing after hybridization (circles).

Figure 7:
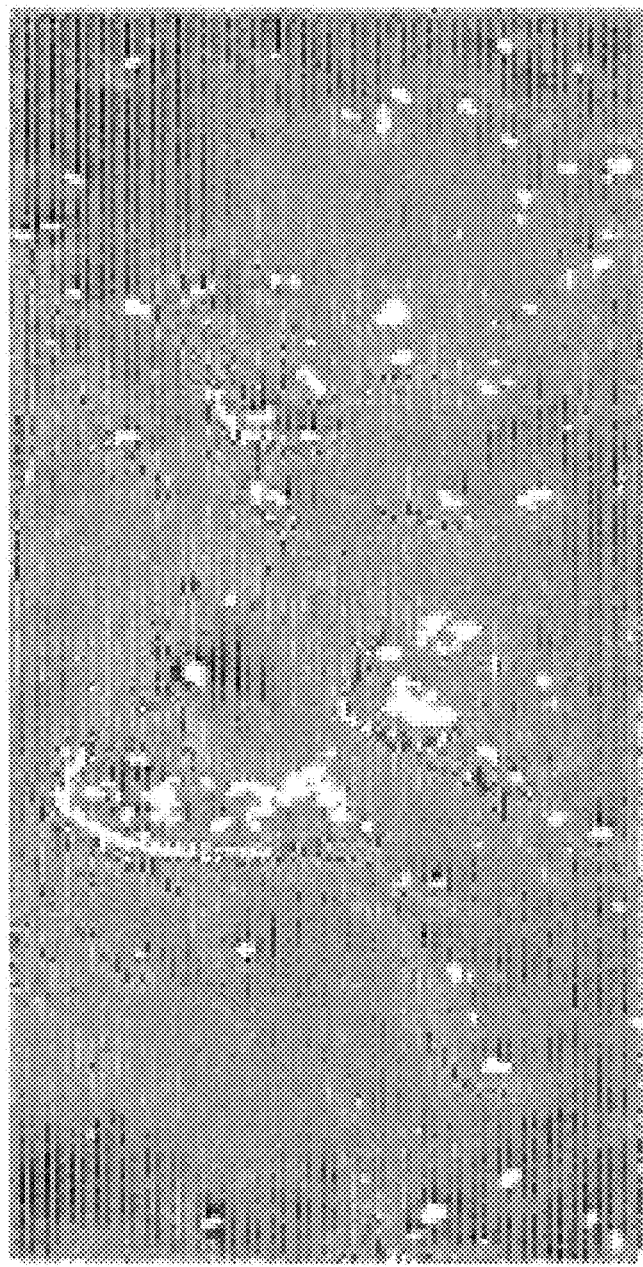

FIG. 7 shows fluorescence measurement after EIS measurement of complementary target (50 nM) binding and 20 nM QD incubation; PMT setting 180.

Figure 8:
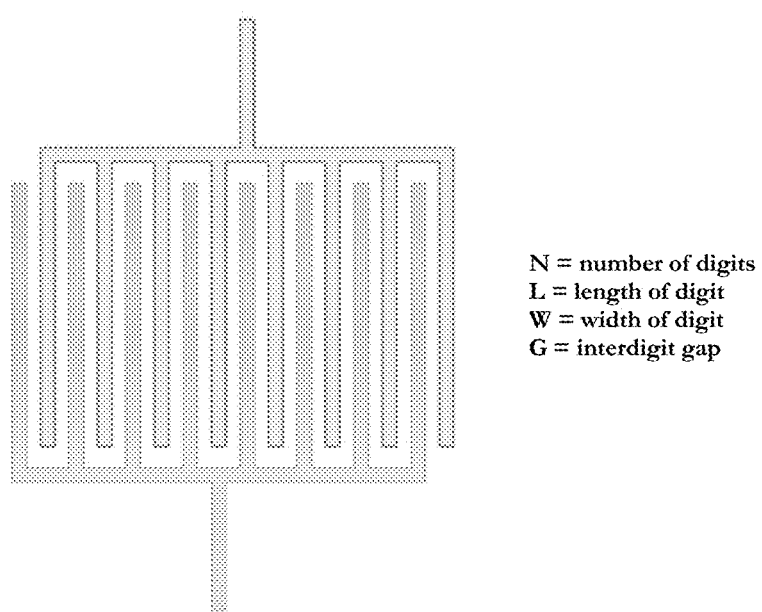

FIG. 8 shows a mask layout of gold interdigitated microelectrode structures, including four device chips, alignment marks and dummy metal lines to speed lift-off processing. The number of digits (N) on each electrode is preferably from 5 to 10. The length of each digit (L) is preferably from 75 to 150 nm. The width of each digit (W) and the width of the gap between each digit (G) is each preferably from 1.5 to 10 nm and W and G are preferably the same.

Figure 9:
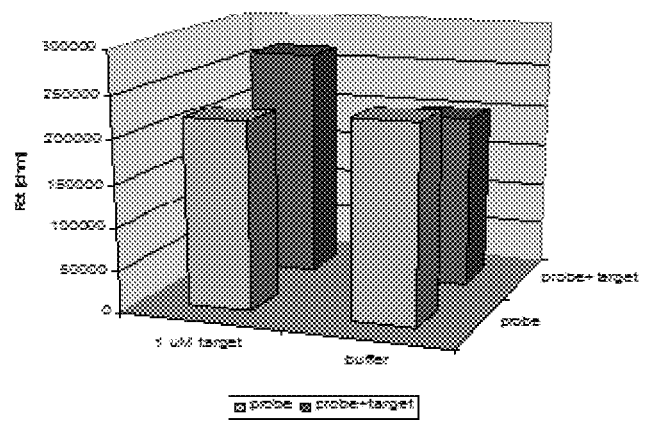
Figure 10:
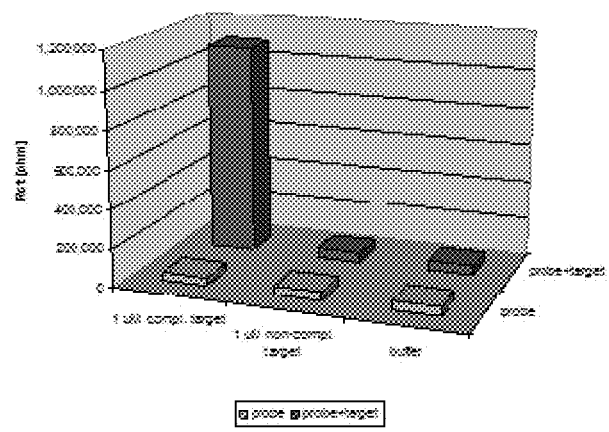

FIG. 9 shows EIS response (electron transfer resistance value (Rct)) with DNA probes before and after hybridisation with 1 µM target, whilst FIG. 10 shows EIS response (Rct) of PNA probes before and after hybridisation with 1 µM target. This big difference in the sensitivity of PNA and DNA probes is caused by the fact that the PNA is a neutral molecule without the negative charged phosphate backbone of DNA molecules. The hybridisation of negatively charged nucleic acid targets cause a big change of the overall charge of the electrode surface. This leads to a large degree of repulsion of the negatively charged electroactive species (ferri/ferrocyanide) used for the faradaic EIS detection, which in turn causes a large increase of the electron transfer resistance value (Rct).

Figure 11:
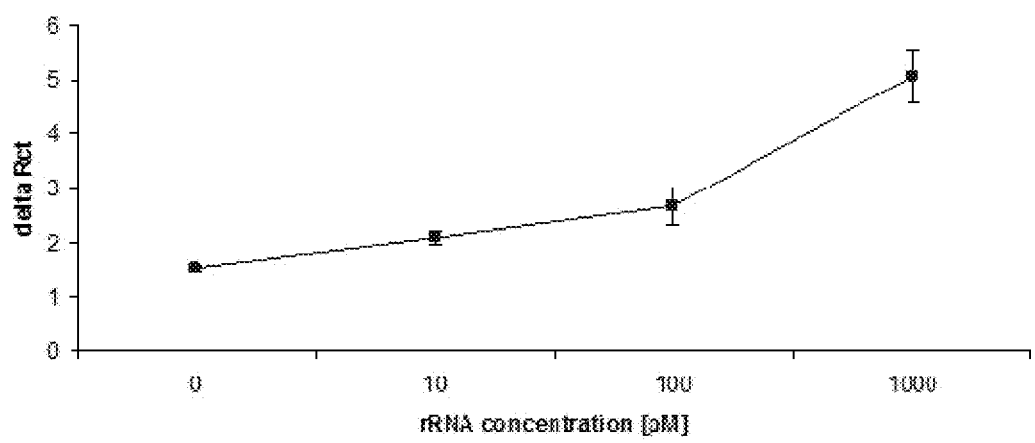

FIG. 11 shows a dose response curve for impedimetric *E. coli* species identification using an *E. coli* specific PNA probe (P51) hybridised with different concentrations of *E. coli* 16S rRNA without prior amplification.

Figure 12:
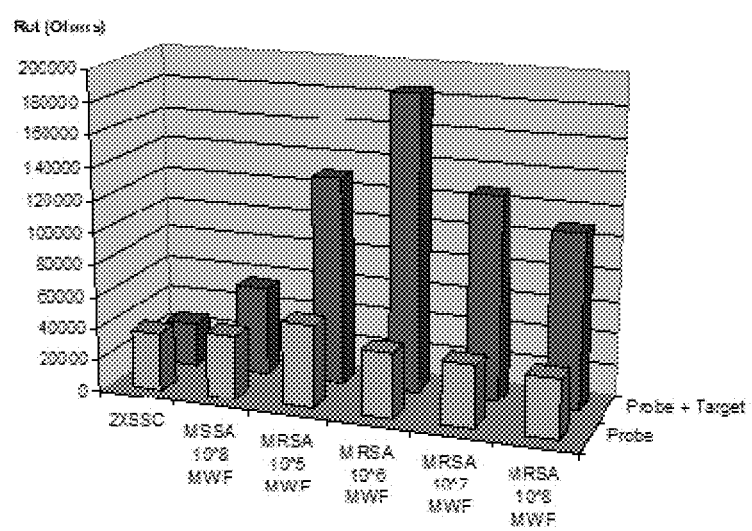

FIG. 12 shows EIS response (electron transfer resistance value (Rct)) before and after hybridisation with genomic DNA extracted from different amounts of methicillin-resistant *staphylococcus aureus* (MRSA) cells ($10^5$-$10^8$ cells/ml mock wound fluid (MWF)) and as control from $10^8$ cells/ml methiccillin-susceptible *S. aureus* (MSSA) spiked into MWF and a buffer control incubation (2×SSC).

Figure 13:
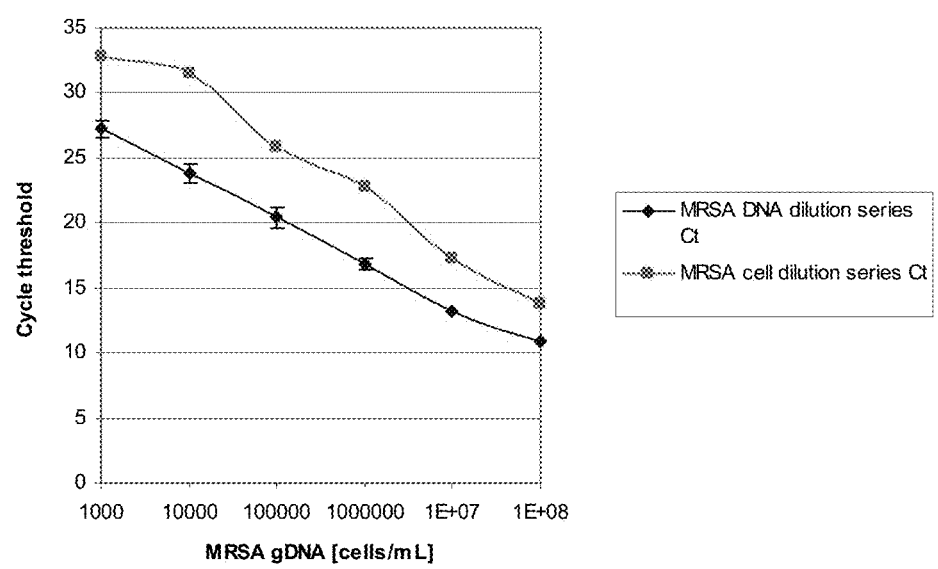

FIG. 13 shows qPCR results from tests conducted with a DNA template recovered from MRSA. The plot shows cell/mL concentrations from WF vs cycle threshold.

Figure 14:
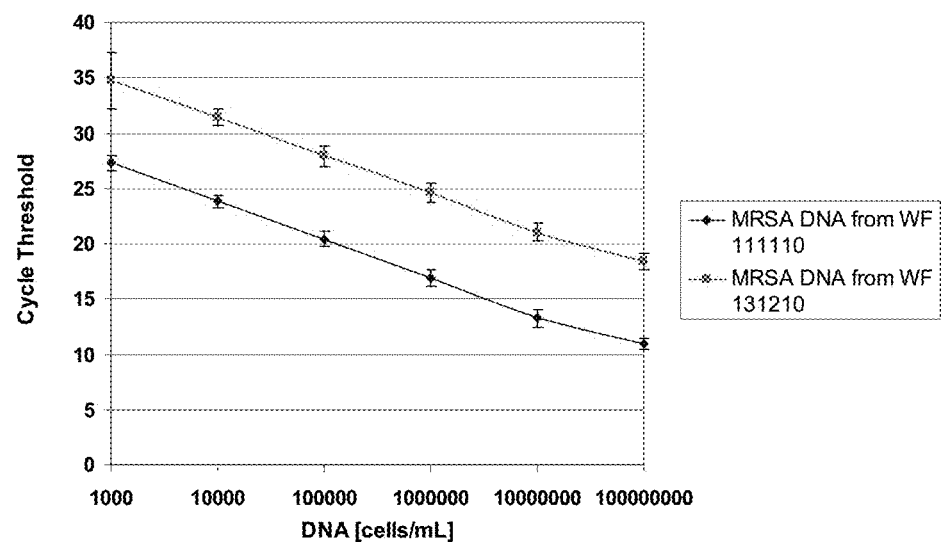

FIG. 14 shows qPCR data demonstrating variation in gDNA yield upon extraction from 108 cells/mL MRSA in wound fluid.

Figure 15A:
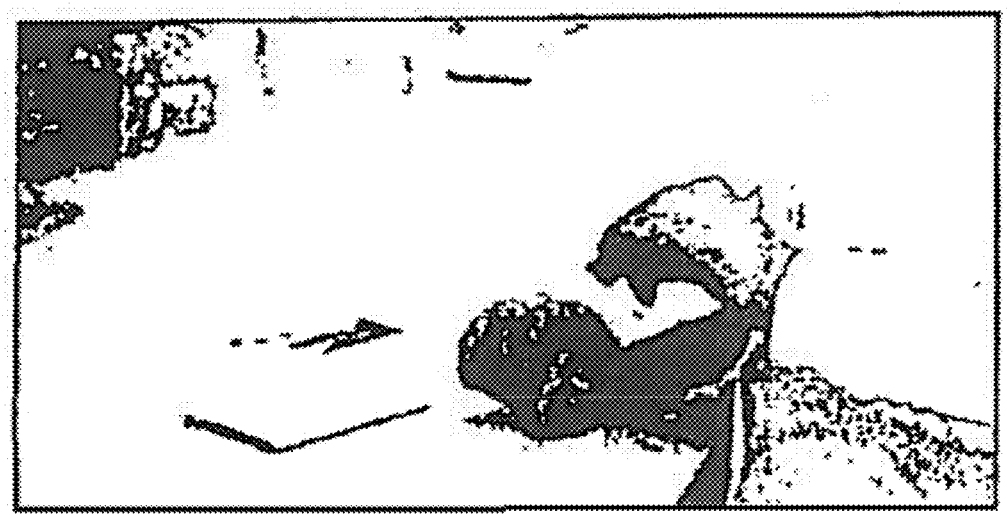
Figure 15B:
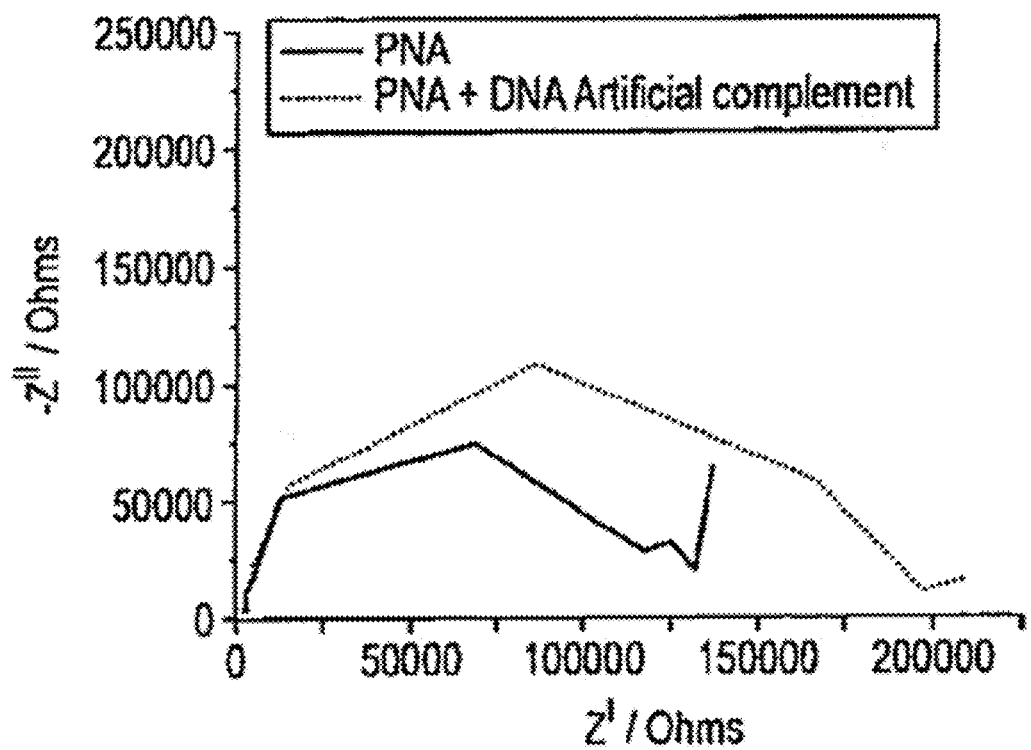

FIG. 15 shows (A) an image of the prototype potentiostat, and (B) a Nyquist plot pre and 10 minutes post introduction of a 23 bp fully complementary oligonucleotide (1 µM).

Figure 16:
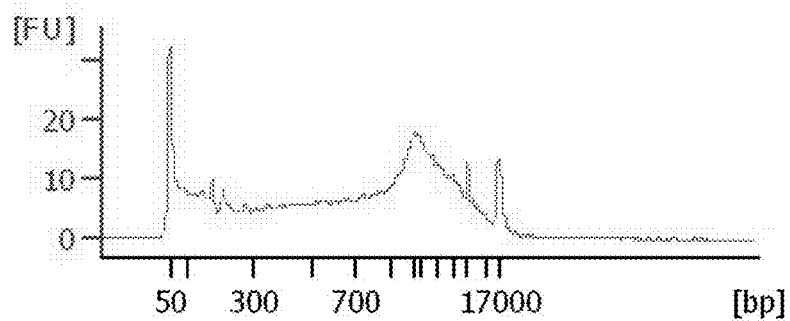
Figure 16:
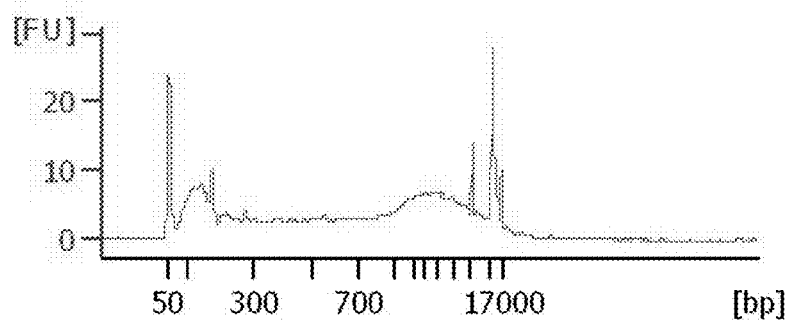
Figure 16:
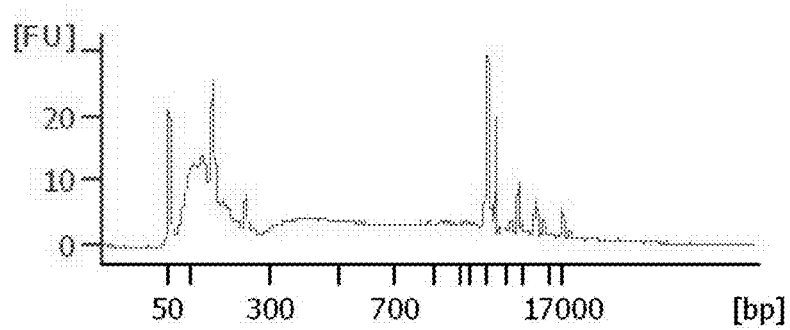

FIGS. 16 A, B & C show bioanalyser data of MRSA gDNA following heat treatment at 95° C. for 0, 1 and 5 mins respectively.

Figure 17:
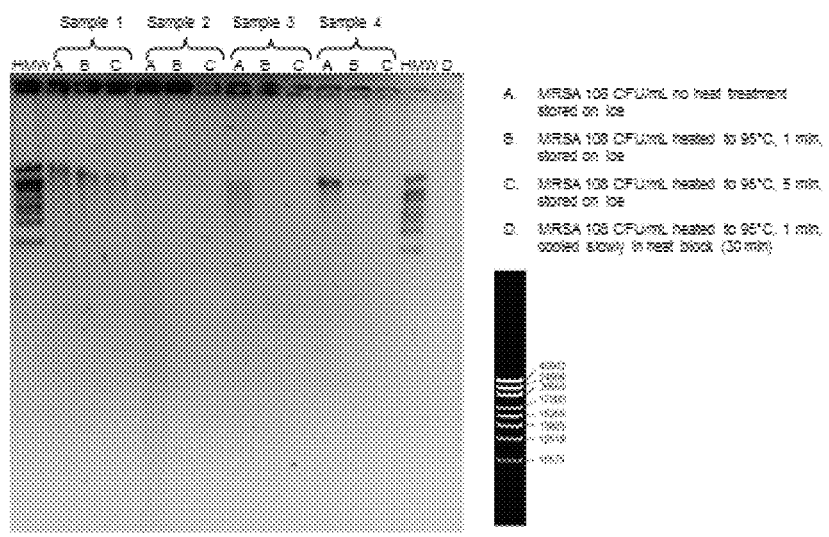

FIG. 17 shows agarose gel electrophoresis of MRSA samples following no heat treatment, 1 min at 95° C. and 5 mins at 95° C.

Figure 18:
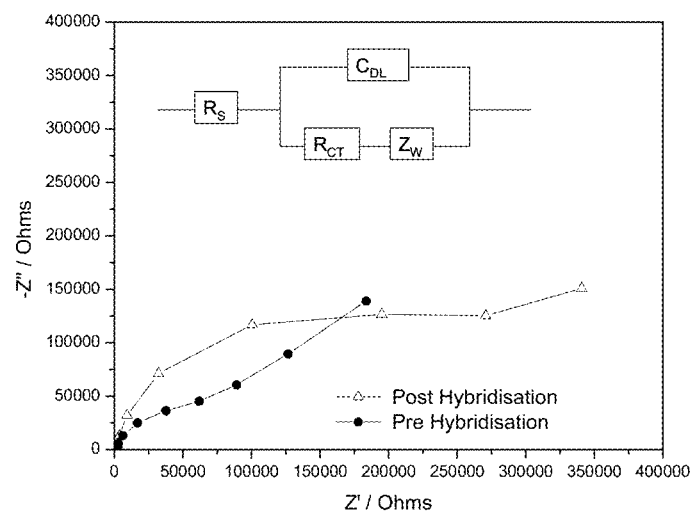

FIG. 18. shows a Nyquist plot of EIS measurements made on a PNA modified gold electrode before and after hybridisation with MRSA gDNA extracted from a suspension of $10^7$ cells/mL and a Randles circuit—RS=solution resistance, CDL=double layer capacitance, RCT=charge transfer resistance and ZW=Warburg diffusion element.

Figure 19:
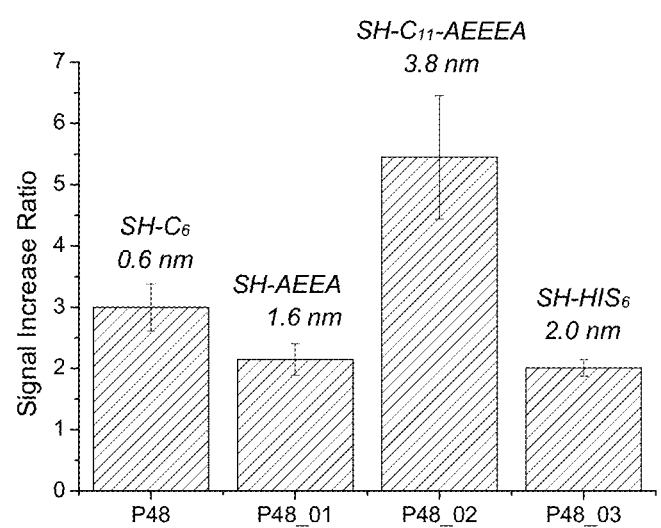

FIG. 19 shows signal Increase Ratio in response to incubating MRSA genomic DNA extracted from suspensions of cells with concentrations of 107 cells/mL with probes containing 4 different spacers; n=3 and error bars=standard deviation.

Figures 20A, 20B, 20C:
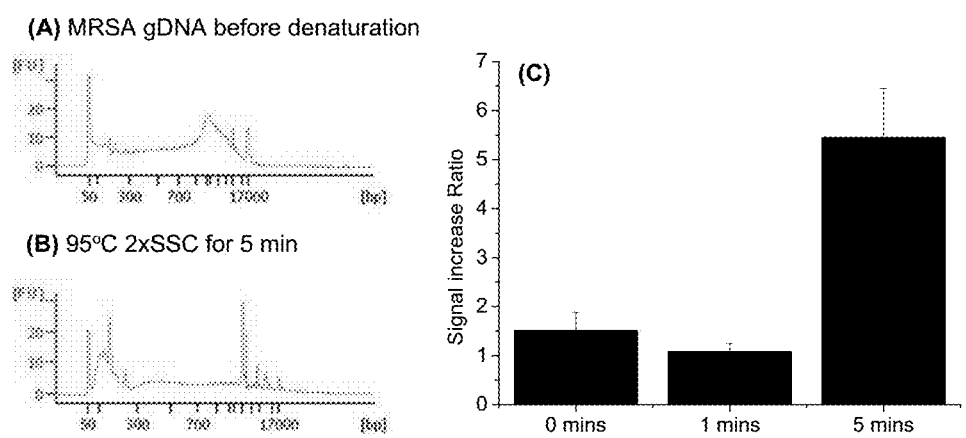

FIG. 20 shows impact of target size on EIS signal: Agilent Bioanalyzer analysis of (A) extracted MRSA gDNA and (B) observable DNA fragmentation when MRSA gDNA was incubated at 95° C. for 5 mins in 2×SSC using DNA 12000 kit; (C) EIS response to incubation with MRSA gDNA following denaturation at 95° C. in 2×SSC for 0, 1 or 5 mins; n=3 and error bars=standard deviation.

FIG. 21 shows (A) dose response curve for MRSA genomic DNA (n=5 and error bars=standard deviation; line=0 MRSA cells/mL+3 standard deviations); and (B) specific and non-specific signal changes from MSSA, *E. coli* and MRSA (n=3 and error bars=standard deviation).

Figure 22:
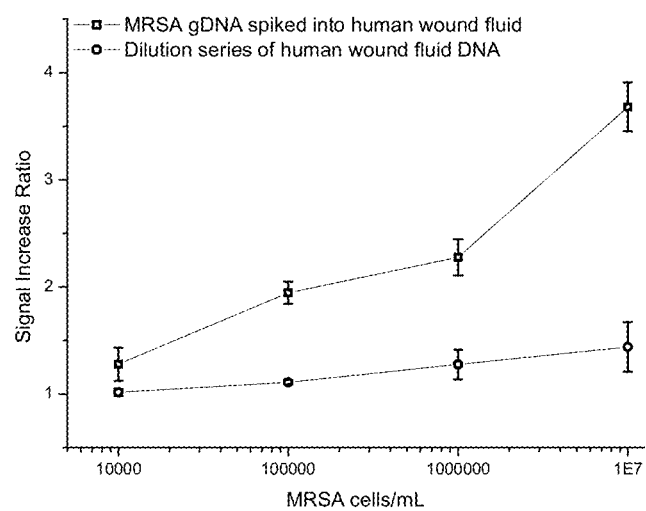

FIG. 22 shows Signal Increase Ratios caused by incubation with gDNA extracted from MRSA cells spiked into human wound fluid and uninnoculated human wound fluid; Signal Increase Ratio measured 10 mins after sample addition; n=3 and error bars=standard deviation.

Figure 23:
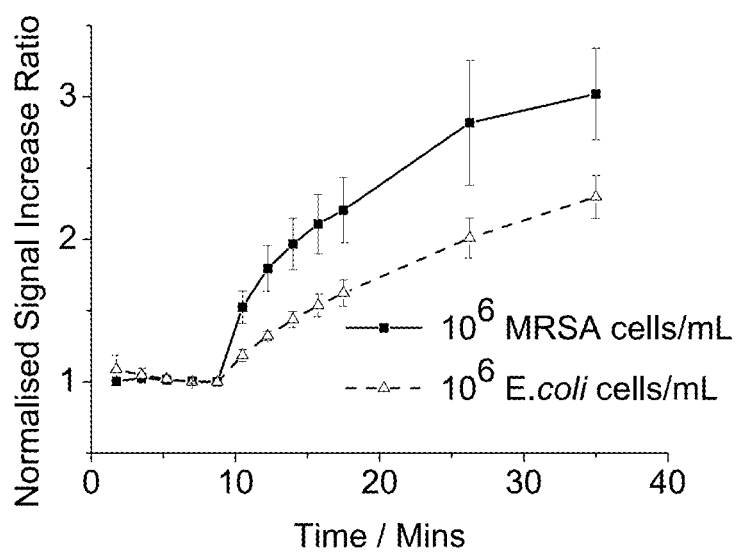

FIG. 23 shows sensor behaviour following exposure to MRSA and *E. coli* gDNA following extraction from suspensions of cells from 106 cells/mL; n=3 and error bars=standard deviation.

The methods of all aspects of the invention have a number of specific advantages over known methods: fast time to result (TTR) in seconds to minutes compatible with near patient environment requirements; wide applicability of approach to different probe-target systems; compatibility with rapid multisine EIS for enhanced data collection; EIS detection compatibility with electronic control and measurement; and label-free detection.

The method of the present invention may be used to detect either a single analyte or a plurality of different analytes simultaneously.

Preferably, the method of the present invention is a label free method, i.e. there is no requirement to label the analyte in order to aid in detection. However, in some circumstances labels may be employed. For example, when the method is used to detect a plurality of different analytes simultaneously, each different analyte may be labelled with one or more different labels relatable to the analyte. Alternatively, multiple analytes may be detected by spatial separation, such as by arraying a set of probes for the analytes on a surface. Detection of a plurality of different analytes is also known as multiplexing.

In the electrochemical detection methods of the invention, the analyte is investigated in solution or suspension in a liquid medium. The liquid medium is not particularly limited provided that it is suitable for analysis using EIS. Preferably the liquid medium comprises an electrolyte to facilitate the EIS measurement. The electrolyte is a solvent or buffer containing inert ions e.g. PBS; typically redox active species are then added at much lower concentrations. The electrolyte is not particularly limited, and may include any electrolyte known in the art. However electrolytes containing transition metal redox systems are preferred, such as Fe(II)/Fe(III) electrolyte systems. $[Fe(CN)_6]^{3-/4-}$ is particularly preferred.

If a plurality of different labels is used to label different analytes, they may be introduced with biotinylated detection probes. Preferably each label has a different oxidation potential for the electrochemical detection method and, therefore, produces different signal peaks in the data obtained. For example, when metal nanoparticles are used as labels for different analytes (see below) different metals with different oxidation potentials may be used for each analyte.

In preferred embodiments the alternating potential applied to the electrode is not especially limited, and depends upon the medium employed. Thus, in practice, the largest possible amplitude for EIS is fixed by the solvent limits (for water around 2 V, giving a rms amplitude of around 1-2 V). Accordingly, in aqueous media the potential may be from +1.0 to +2.0 V, and preferably from +1.2 V to +1.8 V. When using redox species in the system, both oxidised and reduced species are present and this typically results in the use of less than 250 mV amplitude. In more preferred embodiments, the alternating voltage applied between electrodes is of amplitude about 10 mV root mean squared (rms). This enables the response to be linearised for e.g. equivalent circuit analysis. Higher amplitude responses can be used (and if statistical methods are to be employed to extract characteristic signals, they could be different/advantageous).

In a preferred embodiment, the electrical detection method is carried out on a chip. In the multiplexing embodiment of the present invention, where label(s) are used for optical detection, the optical and electrical detection may be carried on one chip when the analyte(s) have been labelled with the different labels simultaneously. Alternatively, where the analyte(s) have been separated into two aliquots and labelled separately they may then be combined after labelling for optical and electrical detection on one chip or optical and electrical detection may be carried out separately on two separate chips.

Using EIS, the amount of analyte present can be quantified. Quantitative data can be obtained from the signal peaks by integration, i.e. determining the area under the graph for each signal peak produced.

Embodiments Employing Labelling

In some preferred embodiments of the present invention, labels are employed, in particular when multiplexing is desirable. The labels referred to are not especially limited, but are preferably selected from nanoparticles, single molecules, intrinsic components of the target such as specific nucleotides or amino acids, and chemiluminescent enzymes. Suitable chemiluminescent enzymes include HRP and alkaline phosphatise. Fluorescent labels are particularly preferred, since optical detection of the labels is readily combined with the electrochemical methods of the invention.

Preferably, the labels are nanoparticles. Nanoparticles are particularly advantageous in these embodiments of the present invention because they operate successfully in electrical detection methods. The proximity of the nanoparticles to the surface is not especially important, which makes the assay more flexible. In a preferred embodiment the nanoparticles comprise a collection of molecules because this gives rise to greater signal in optical and electrical detection methods than when single molecules are used.

Preferably the nanoparticles are selected from metals, metal nanoshells, metal binary compounds and quantum dots. Examples of preferred metals or other elements are gold, silver, copper, cadmium, selenium, palladium and platinum. Examples of preferred metal binary and other compounds include CdSe, ZnS, CdTe, CdS, PbS, PbSe, HgI, ZnTe, GaAs, HgS, CdAs, CdP, ZnP, AgS, InP, GaP, GaInP, and InGaN.

Metal nanoshells are sphere nanoparticles comprising a core nanoparticle surrounded by a thin metal shell. Examples of metal nanoshells are a core of gold sulphide or silica surrounded by a thin gold shell.

Quantum dots are semiconductor nanocrystals, which are highly light-absorbing, luminescent nanoparticles (West J, Halas N, Annual Review of Biomedical Engineering, 2003, 5: 285-292 "Engineered Nanomaterials for Biophotonics Applications: Improving Sensing, Imaging and Therapeutics"). Examples of quantum dots are CdSe, ZnS, CdTe, CdS, PbS, PbSe, HgI, ZnTe, GaAs, HgS, CdAs, CdP, ZnP, AgS, InP, GaP, GaInP, and InGaN nanocrystals.

Any of the above labels may be attached to an antibody.

The size of the labels is preferably less than 200 nm in diameter, more preferably less than 100 nm in diameter, still more preferably 2-50 nm in diameter, still more preferably 5-50 nm in diameter, still more preferably 10-30 nm in diameter, most preferably 15-25 nm.

When the method of the present invention is for detecting a plurality of analytes, each different analyte is labelled with one or more different labels relatable to the analyte. In this aspect of the invention, the labels may be different due to their composition and/or type. For example, when the labels are nanoparticles the labels may be different metal nanoparticles. When the nanoparticles are metal nanoshells, the dimensions of the core and shell layers may be varied to produce different labels. Alternatively or in addition, the labels have different physical properties, for example size, shape and surface roughness. In one embodiment, the labels may have the same composition and/or type and different physical properties.

The different labels for the different analytes are preferably distinguishable from one another in the optical detection method and the electrical detection method. For example, the labels may have different frequencies of emission, different scattering signals and different oxidation potentials.

In embodiments of the present invention where labelling is employed, such as in multiplexing, the method typically comprises a further initial step of labelling the analyte with one or more labels to form the labelled analyte.

The means for labelling the analyte are not particularly limited and many suitable methods are well known in the art. For example, when the analyte is DNA or RNA it may be labelled by post-hybridization labelling at ligand or reactive sites or "sandwich" hybridization of unlabelled target and label-oligonucleotide conjugate probe (Fritzsche W, Taton T A, Nanotechnology 14 (2003) R63-R73 "Metal nanoparticles as labels for heterogeneous, chip-based DNA detection").

Figure 2:
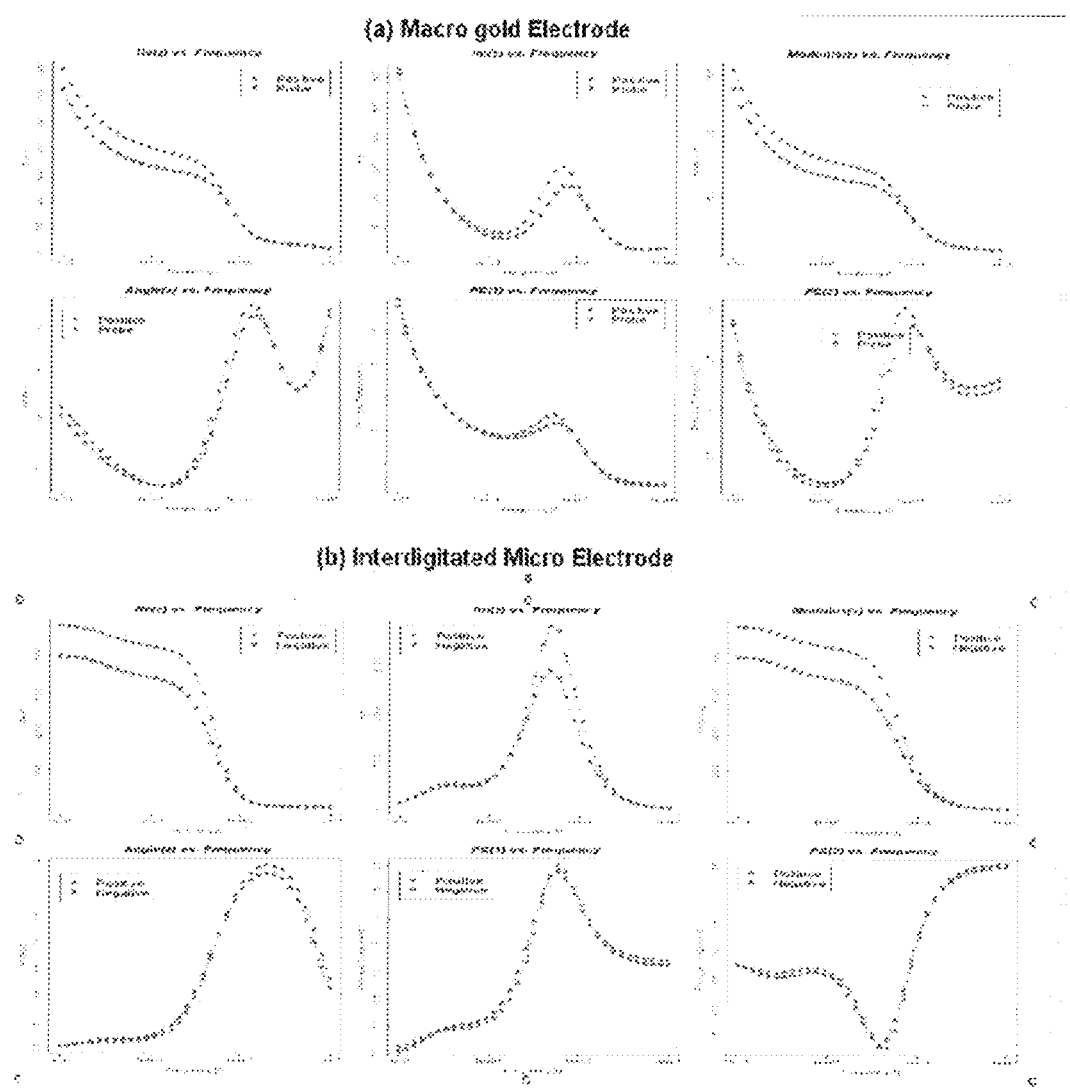
FIG. 2 shows plots of real component (x), imaginary component (y), modulus (r), angle (θ), Principal component 1, and Principal component 2 against frequencies for the data for positive controls and immobilised probes for both macro and interdigitated electrodes.

Many different methods are known in the art for conjugating oligonucleotides to nanoparticles, for example thiol-modified and disulfide-modified oligonucleotides spontaneously bind to gold nanoparticles surfaces, di- and tri-sulphide modified conjugates, oligothiol-nanoparticle conjugates and oligonucleotide conjugates from Nanoprobes' phosphine-modified nanoparticles (see FIG. 2 of Fritzsche W, Taton T A, Nanotechnology 14 (2003) R63-R73 "Metal nanoparticles as labels for heterogeneous, chip-based DNA detection").

In one embodiment, both DNA or RNA strands may be biotinylated. The biotinylated target strand may be hybridized to oligonucleotide probe-coated magnetic beads. Streptavidin-coated gold nanoparticles may then bind to the captured target strand (Wang J, Xu D, Kawde A, Poslky R, Analytical Chemistry (2001), 73, 5576-5581 "Metal Nanoparticle-Based Electrochemical Stripping Potentiometric Detection of DNA hybridization"). The magnetic beads allow magnetic removal of non-hybridized DNA.

To perform the EIS step, a pair of electrodes must be used. These are not especially limited, but in typical embodiments they are screen-printed or macro gold electrodes, or alternatively interdigitated electrodes (LEDs). The material of the electrodes is not especially limited, provided that it does not interfere with the chemical processes taking place when the nucleic acid analyte binds to the PNA probes on the electrode surface. Typically the electrodes are formed from an inert metal, such as gold. A mask layout of gold interdigitated microelectrode structures, including four device chips, alignment marks and dummy metal lines to speed lift-off processing is shown in FIG. 8. The number of digits (N) on each electrode is preferably from 5 to 10. The length of each digit (L) is preferably from 75 to 150 µm. The width of each digit (W) and the width of the gap between each digit (G) is each preferably from 1.5 to 10 µm and W and G are preferably the same.

The present invention will be described further by way of example only.

EXAMPLES

Example 1—Investigating EIS Parameters for Multiple Frequency Analysis

In order to investigate the optimum parameters to use in the method one aspect of the invention, any EIS set-up may be employed. However, typically the electrodes, electrolytes, liquid medium, analytes (and probes if they are to be used) that will be involved in the final analysis will be employed to ensure that the parameters are as close to optimal as possible.

In this Example, probe-target hybridisation on commercial gold interdigitated electrodes (IDEs) from Abtech was studied. An electrochemical cleaning cycle was utilised, applying to both electrodes in the IDE pair a linear potential sweep between −0.6 V and +1.65 V versus Ag/AgCl in 50 mM aqueous $H_2SO_4$ solution at a sweep rate of 50 mVs for 30-40 complete cycles, until a stable cyclic voltammogram (CV) characteristic of clean gold electrodes was seen. Before preparing the DNA (69 mer ITI 021) solution, the DNA probes were purified by passing them through a MicroSpin™ G-25 column (Amersham Biosciences, Buckinghamshire, UK) after cleavage of the disulfide protected nucleotides with 5 mM of TCEP solution.

Figure 1:
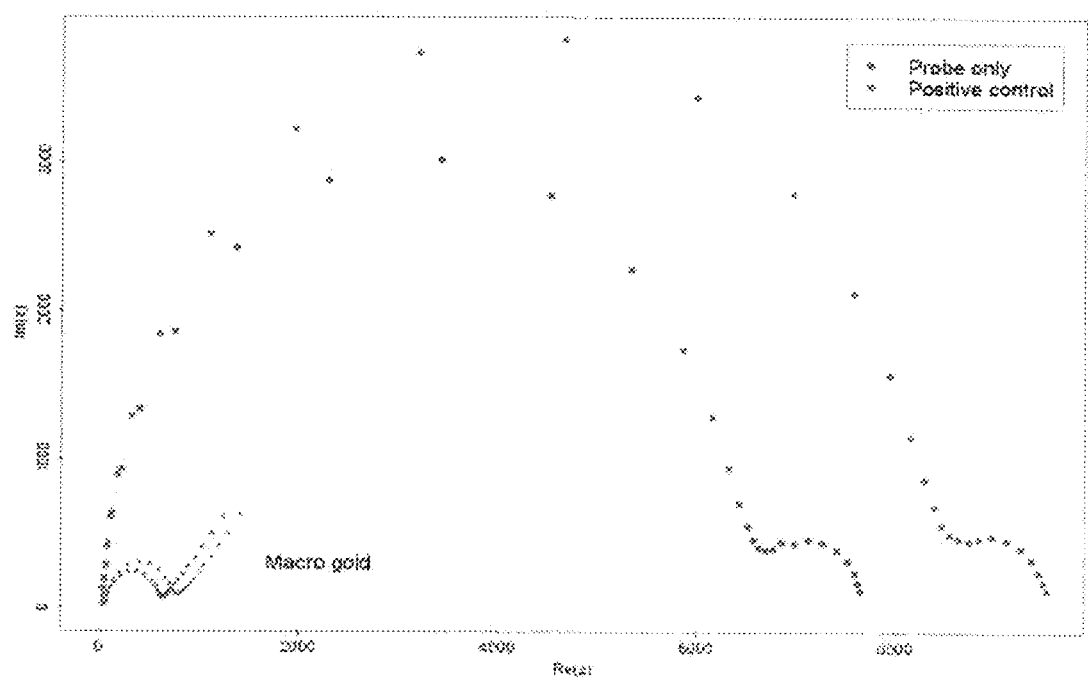
FIG. 1 shows typical Nyquist plots of EIS data from Macro gold (small Z values) and interdigitated micro (IME) electrodes.

Nyquist plots of a large frequency range for EIS for both macro gold and interdigitated micro (IME) electrodes were plotted, and these are shown in FIG. 1; each shows distinct signals for complementary target binding.

The differences between the positive control (probe with complementary target bound) and negative control (probe only or probe with non-complementary target) were compared in terms of parameters derived from the complex impedance, which can be written as x+iy, where i is $(-1)^{1/2}$%. These are:

Real component (x)
Imaginary component (y)
Modulus or absolute value $[r=|z|=(x^2+y^2)^{1/2}]$
Angle $[\theta=\tan-1(y/x)]$
Principal component 1
Principal component 2

These differences were investigated in terms of each of these quantities by plotting them against the logarithm of frequency (see FIG. 2).

FIG. 2 shows that for both large (macro) and small (interdigitated micro) electrodes, the real component and modulus provide similar information and best discriminate the EIS signal from the positive controls and immobilised probes, particularly at the lower end of the frequency range. The imaginary component best discriminates the EIS signal in the middle of the frequency range.

For optimising the time to result (TTR), the present invention selects the most useful range of frequency and smallest number of measurements that best discriminates between the different EIS data for all experimental conditions, and does not require employing fitting models such as equivalent circuits. Statistical analysis in this Example determined a 7-point optimal frequency range for both macro gold and interdigitated micro electrodes (IME) using the fold change between the EIS signal of the positive control and the immobilised probes.

The results are summarised in Table 1.

TABLE 1

Summary results for 7-point optimal frequency range (in Hz) for Macro Electrode and Interdigitated Micro Electrode based on complementary hybridisation vs. immobilised probe without target comparison.

| Signal Type | No. of Points | Optimum Range for Macro Electrode | Optimum Range for IME Electrodes |
|---|---|---|---|
| Modulus | 7 | [4, 44] | [3, 30] |
| Real component | 7 | [3, 44] | [3, 30] |
| Imaginary Component | 7 | [30, 338] | [13, 150] |

It is notable that, for both types of electrodes, the modulus data and real component give a very similar range of optimal frequencies for EIS measurement, spanning around a decade of frequency. For both types of electrode, the imaginary component gives optimal signals at slightly higher frequencies than that for real and modulus data, again spanning a decade of frequencies. The very large changes in the electrode dimensions from macro to IME have had little effect on the optimum frequency range for measurement, consistent with the response being largely independent of electrode area, which simplifies EIS measurement. Differential analysis of complementary versus mock hybridisation using fold-change gave a similar optimal frequency range to that of complementary hybridisation vs. immobilised probe signals (Table 2), confirming that the same measurement range can be used.

TABLE 2

7-point optimal frequency range in Hz for Macro Gold Electrode based on complementary versus mock hybridisation comparison.

| Signal Type | No. of points | Optimal range |
|---|---|---|
| Modulus | 7 | [4, 44] |
| Real component | 7 | [3, 30] |
| Imaginary Component | 7 | [20, 255] |

To enable these data to be obtained rapidly, multisine techniques have been employed to apply the required multiple frequencies simultaneously, with FFT to analyse the results and extract these data. FIG. 3 shows a comparison of the EIS Nyquist plot for the previously used method of sequential application of single sines to the measured responses for 5 multisine (over one decade of frequency) and 15 multisine (over two decades of frequency) EIS measurements for a protein macroelectrode experimental system. Experimental data collection, analysis and display was achieved on a PC in several minutes for sequential application, around 7 seconds for 5 sines and around 23 seconds for 15 sines. The component frequencies for this multisine experiment have been selected to span the frequency range determined by statistical analysis, which spans the semicircular charge transfer feature in the EIS Nyquist plot shown. The extremely close correspondence of all data (typically to within 0.05%) indicates that the multisine EIS approach leads to more rapid EIS parameter extraction compatible with EIS measurement and analysis (and hence a TTR) of seconds, without compromising the accuracy of measurement.

Example 2—Investigating Real Time Kinetics Measurement Using EIS

In this Example, the kinetics of probe-target hybridisation on commercial gold IDEs from Abtech were studied. An electrochemical cleaning cycle was utilised, applying to both electrodes in the IDE pair a linear potential sweep between −0.6 V and +1.65 V versus Ag/AgCl in 50 mM aqueous $H_2SO_4$ solution at a sweep rate of 50 mVs for 30-40 complete cycles, until a stable cyclic voltammogram (CV) characteristic of clean gold electrodes was seen. Before preparing the DNA (69 mer ITI 021) solution, the DNA probes were purified by passing them through a MicroSpin™ G-25 column (Amersham Biosciences, Buckinghamshire, UK) after cleavage of the disulfide protected nucleotides with 5 mM of TCEP solution.

Immediately after cleaning, thiol-DNA probe layers were immersed in a 10 μM DNA solution in 2×SSC buffer and 10 mM of each of $[Fe(CN)_6]^{3-}$ and $[Fe(CN)_6]^{4-}$ (10 mM [Fe(CN)$_6$]$^{3-/4-}$) at room temperature. The EIS measurement was started as soon as the electrode was immersed in the DNA solution and was left to run for 3-4 h. As previously, a 10 mV RMS amplitude sinusoidal voltage was applied between the electrodes in the IDE pair at a DC voltage of 0 V throughout in these experiments, as the presence of equal concentrations of $[Fe(CN)_6]^{3-}$ and $[Fe(CN)_6]^{4-}$ ensured that the DC potential of each electrode was pinned at the reduction potential of $[Fe(CN)_6]^{3-/4-}$. Then, the modified surface was washed with 2×SSC for a few minutes and blocked with MCH 1 mM in water at room temperature for 30 minutes. After washing for 10-20 minutes in 2×SSC buffer, the electrode EIS signal was measured again in 10 mM $[Fe(CN)_6]^{3-/4-}$ 2×SSC buffer to check for changes after the blocking step. The electrodes were then immersed in the target (complementary or not) DNA dissolved in 2×SSC and containing 10 mM $[Fe(CN)_6]^{3-/4-}$ to allow EIS measurements, again at 0 V DC.

FIG. 4 shows typical impedance plots of these 69-mer thiol-DNA modified probe electrodes, before and after hybridisation with 1 μM of complementary target (ITI 025). The high frequency semicircle is the common feature for both macro and IDE electrodes, and gives information on the charge transfer through the probe film layer at the electrode surface. After addition of 1 μM of complementary target the diameter of this high frequency semicircle increases, as expected, due to complementary target-probe binding in the probe layer, whilst the lower frequency diffusion feature remains essentially unchanged, indicating (as expected) little effect on diffusion between the electrodes.

FIG. 5 shows another example of IDEs prepared in the same way. In this case, after the blocking, a negative control was carried out: for a few hours the EIS was monitored in a solution containing 1 μM non complementary (ITI 012) target and 10 mM $[Fe(CN)_6]^{3-/4-}$ in 2×SSC. As expected, no changes were observed in the impedance signal, indicating no non complementary target probe binding. After this the electrode was rinsed in 2×SSC buffer and the response measured in a solution of 1 nM complementary target DNA and 10 mM $[Fe(CN)_6]^{3-/4-}$ in 2×SSC. After 1 h, when the response was stable, the electrode was immersed in 50 nM target solution and measured overnight. The difference between probe and 1 nM target is small but significant, whilst it is easily seen for 50 nM. Thus EIS is probing complementary target binding using the established method of waiting for equilibration.

FIG. 6 now shows typical EIS measurements made in real time: the parameter sensitive to probe film formation and probe-target hybridisation is the electron transfer resistance, Ret, for $[Fe(CN)_6]^{3-/4-}$, which has been calculated from finding the width of the semicircular feature in the Nyquist plot of each of the EIS spectra. This has been plotted (as Ret for electron transfer) as function of time in this Figure.

These data are rich in information, and show the establishment of a probe film (diamonds), blocking and washing (squares) and the kinetics of probe-target hybridisation (triangles). When the gold electrode is exposed to probe film solution (diamonds) the value of Ret rises over the first hour or so due to probe film formation, then falls to a steady-state value after 3 4 hours, indicating a stable surface film. This is confirmed by removing the probe solution and washing, as there is little change in the observed value. Adding mercaptohexanol (MCH) to block any remaining gold surface also causes little change in resistance, as does measuring the resistance over time in buffer with $[Fe(CN)_6]^{3-/4-}$ (squares), which again indicates a stable probe film. Having established a stable probe film, the kinetic technique is then used to monitor probe-target binding in the solution containing complementary target and ferri/ferrocyanide. On exposing the probe film to this solution (triangles), an immediate increase in Ret is seen due to complementary target probe binding. The initial response is immediate, with the first point showing an increase in Ret and with the value more than doubling within the first hour. This method enables the measurement of EIS response kinetically every few seconds (see multisine IDF). The rate of increase in probe-target binding would typically be expected to be first order in (and certainly dependent on) target concentration; therefore analysis of the rate of rise of EIS is then possible on the seconds to minutes timescale to give target concentration. It is satisfactory that the impedance increases more slowly over several hours after this, showing the long-time approach to an equilibrium response which limits the TTR of equilibrium measurement. On removing the target solution, washing and then measuring the response in buffer with $[Fe(CN)_6]^{3-/4-}$ (circles), after a transient change in Ret the value returns initially to that observed previously, showing that the response is indicative of probe-target binding.

In order to confirm that probe layer formation and hybridisation had occurred on the gold electrode, biotin-labelled target was used and then incubated (for 1 h at room temperature) with streptavidin-labelled Qdots (20 nM in QD buffer).

It is clear from the resulting fluorescence image (FIG. 7) that as expected the regions of highest fluorescence intensity are on the gold fingers of the IDE. This confirms the enhancement of Ret observed after hybridisation is due to probe-target hybridisation in a film on the gold IDE surfaces.

Example 3—Comparison of DNA and PNA Probes

EIS Protocol for DNA Probes (FIG. 9)

After cleaning, the gold macrodisk electrodes were incubated with a solution of 200 nM thiol-modified oligonucleotide solution+800 mM mercaptohexanol in 1 M NaCl+5 mM $MgCl_2$+1 mM EDTA for 16 h at 30° C. Thiol-modified oligonucleotides were provided from the manufacturer as disulfides with a mercaptoethyl protection group. This mercaptoethyl protection group was removed prior immobilisation by incubation with 5 mM TCEP for 30 min followed by gel extraction clean-up with Illustra spin G-25 micro columns (GE Healthcare). The electrodes with immobilised probe were blocked with an aqueous solution of 1 mM mercaptohexanol for 1 h at 30° C. Then the electrodes were washed with the immobilisation buffer (1 M NaCl+5 mM $MgCl_2$+1 mM EDTA), 1×PBS and 1×PBS+10 mM EDTA for 10 min each.

EIS measurements were performed with a three electrode system with an Ag/AgCl reference electrode and a platinum wire counter electrode (both from Metrohm (Runcorn, UK) connected to an Autolab potentiostat (Metrohm, Runcorn, UK) before and after hybridisation. EIS measurements were performed at 0.24 V with in amplitude of 10 mV at a frequency range between 100,000 Hz-0.1 Hz (15 frequencies) in 1 mM $K_3[Fe(CN)_6]$+60 mM KCl. Electrodes were hybridised with 1 µM complementary artificial target (20 mer oligonucleotide) in 2×SSC for 2 h at 50° C. and with the hybridisation buffer alone without target (negative control), respectively. After hybridisation electrodes were washed with 2×SSC, 0.2×SSC solution and the EIS measurement buffer for 10 min each.

EIS Protocol for PNA Probes (FIG. 10)

After cleaning the gold macrodisk electrodes were incubated with a solution of 1.5 µM thiol-modified PNA solution+30 µM mercaptohexanol in 50% (v/v) DMSO for 16 h at 30° C. after incubation at 30° C. for 10 min. Electrodes were rinsed in 50% (v/v) DMSO and incubated in 1 mM mercaptohexanol in 50% (v/v) DMSO for 1 h at 30° C. Then the electrodes were washed with 50% (v/v) DMSO and the EIS measurement buffer (0.1 mM $K_3[Fe(CN)_6]$+10 phosphate buffer for 10 min each.

EIS measurements were performed with a three electrode system with an Ag/AgCl reference electrode and a platinum wire counter electrode (both from Metrohm (Runcorn, UK) connected to an Autolab potentiostat (Metrohm, Runcorn, UK) before and after hybridisation. EIS measurements were performed at 0.24 V with in amplitude of 10 mV at a frequency range between 100,000 Hz-0.1 Hz (15 frequencies) in 0.1 mM $K_3[Fe(CN)_6]$+10 phosphate buffer.

Electrodes were hybridised with 1 µM complementary artificial target (20 mer oligonucleotide) and 1 µM non-complementary artificial target (20 mer oligonucleotide) in 2×SSC for 2 h at 50° C. and with the hybridisation buffer alone without target (negative control), respectively. After hybridisation electrodes were washed with 2×SSC, 0.2×SSC solution and the EIS measurement buffer for 10 min each.

Example 4—Detection of *E. coli* rRNA (FIG. 11)

EIS Protocol for RNA Detection with PNA Probes

After cleaning the gold macrodisk electrodes were incubated with a solution of 1.5 µM thiol-modified PNA solution+30 µM mercaptohexanol in 50% (v/v) DMSO for 16 h at 30° C. after incubation at 30° C. for 10 min. Electrodes were rinsed in 50% (v/v) DMSO and incubated in 1 mM mercaptohexanol in 50% (v/v) DMSO for 1 h at 30° C. Then the electrodes were washed with 50% (v/v) DMSO and the EIS measurement buffer (0.1 mM $K_3[Fe(CN)_6]$+10 phosphate buffer for 10 min each.

EIS measurements were performed with a three electrode system with an Ag/AgCl reference electrode and a platinum wire counter electrode (both from Metrohm (Runcorn, UK) connected to an Autolab potentiostat (Metrohm, Runcorn, UK) before and after hybridisation. EIS measurements were performed at 0.24 V with in amplitude of 10 mV at a frequency range between 100,000 Hz-0.1 Hz (15 frequencies) in 0.1 mM $K_3[Fe(CN)_6]$+10 phosphate buffer.

Electrodes were hybridised with nucleic acid target solution in 2×SSC for 2 h at 50° C. Ribosomal 16S RNA extracted from *E. coli* was applied as full length rRNA. After hybridisation electrodes were washed with 2×SSC, 0.2×SSC solution and the EIS measurement buffer for 10 min each.

RNA Extraction Protocol

Inoculate 2.5 mL Luria-Bertani (LB) medium (10 g/L Bacto-tryptone, 5 g/L yeast extract, 10 g/L NaCl) with an *E. coli* DH10β colony from a LB agar plate and incubate for 16 h at 37° C. in a shaking incubator.

Prepare TE buffer containing 15 mg/ml lysozyme.

Add 2 volumes of RNA protect Bacteria Reagent into 1 volume of bacterial culture and vortex immediately, and then incubate for 5 min at room temperature Centrifuge for 10 min at 13,500 rpm and remove supernatant Add 10-20 µl QIAGEN Proteinase K to 200 µL TE buffer containing lysozyme and re-suspend the pellet by pipetting Incubate on roller mixer at room temperature for 30 min Add 700 µL buffer RLT and vortex vigorously. If there is a white precipitate centrifuge at 13,500 rpm and use supernatant in following steps Add 500 µL 100% ethanol and shake vigorously Transfer 700 µl lysate to an RNeasy Mini spin column in a 2 ml collection tube and centrifuge for 30 s at 13,500 rpm. Discard flow through and add remainder of sample and centrifuge again. Discard flow through Add 350 µL of RW1 to the spin column and centrifuge for 30 s at 13,500 rpm and discard flow through Mix 10 µl DNase I stock solution 70 µl Buffer RDD, invert and spin down. Add the 80 µl of the solution directly to the column and incubate at room temperature 15 min Add 350 µl Buffer RW1 to the RNeasy spin column and incubate for a further 5 min Centrifuge for 30 s@13,500 rpm, discard the flow-through Transfer the column to a 2 ml tube and add 500 uL RPE buffer to the column. Centrifuge 30 s@13,500 rpm Repeat this step with 2 min centrifugation@13,500 rpm Elute rRNA in 30 µL deionised water and quantify using the nanodrop.

Example 5—Detection of MRSA gDNA Using Method of Invention (FIG. 12)

Gold electrodes were used in a three electrode system with a platinum counter and silver/silver chloride reference electrode. The gold electrode surface was cleaned by cyclic voltammetry in 0.1 M $H_2SO_4$, scanning the potential between 0 and 1.6 V 10 times and between 0 and 1.3 V 10 times at a scan rate of 0.1 V/s. In the case of gold macro electrodes additional cleaning steps were included in the protocol which preceded cyclic voltammetry and these were 1) electrode polishing with alumina slurry and 2) submersion of electrodes in piranha solution for 10 mins.

Once clean the gold electrode was incubated for 16 h with a solution containing 1.5 µM thiol-modified PNA solution+ 30 µM mercaptohexanol in 50% (v/v) DMSO. Blocking was then carried out by incubating the electrode in 1 mM mercaptohexanol for 1 h. Upon completion of blocking the electrode was washed in 50% DMSO for 2 h and in EIS measurement buffer (0.1 mM $K_3[Fe(CN)_6]$+0.1 mM $K_4[Fe(CN)_6]$+pH 7.0 10 mM phosphate buffer).

To obtain methicillin resistance *S. aureus* (MRSA) and methicillin susceptible *S. aureus* (MSSA) gDNA bacteria were sub cultured onto Columbia blood agar and incubated overnight at 37° C. in a $CO_2$ atmosphere. Cells were inoculated into saline and the optical density measured using a Densicheck (bioMerieux). This gave values in McFarland units, proportional to the cellular concentration of bacteria in the suspension. A bacterial cell suspension in saline solution or mock wound fluid (MWF) of approximately $10^8$ cells/mL was produced in this way and ten-fold dilutions ranging down to $10^2$ cells/mL prepared from this suspension.

The bacterial cells were pelleted by centrifuging 1 mL of the suspension at 5000×g for 10 mins. The supernatant was discarded and the bacterial pellet re-suspended in 200 µL of enzymatic lysis buffer (2×TE Buffer, 1.2% Triton X, 50 µg/mL Lysostaphin), before incubating for 30 mins at 37° C. 200 µL of bacterial lysate was added to 20 µL Proteinase K and DNA extracted using the bioMerieux NucliSens easy-MAG automated platform. Guanidine Thiocyanate was the active chaotropic agent in the lysis buffer, acting as a protein denaturant in the purification and extraction of nucleic acids from cellular material. The purified nucleic acid solution was then removed from the vessel without dislodging the magnetic silica pellet—DNA was eluted in 100 µL of water.

EIS measurements were performed at a DC potential of 0.24 V with an amplitude of 10 mV rms using a frequency range between 100,000 Hz-0.1 Hz (15 frequencies) in 0.1 mM $K_3[Fe(CN)_6]$+0.1 mM $K_4[Fe(CN)_6]$+10 mM phosphate buffer. The MRSA gDNA sample was prepared by mixing 45 µL of sample with 5 µL of 20×SSC and then heating at 95° C. for 5 mins, storing on ice for 2 mins and heating at 25° C. for 5 mins. The electrode was incubated with the sample for 2 h at 55° C. with shaking (650 rpm). Following incubation with sample, electrodes were washed with 2×SSC, 0.2×SSC and EIS measurement buffer for 10 mins in each. EIS measurements were performed pre and post hybridisation.

Preparation of Mock Wound Fluid (MWF)

Ringer's (Krebs) Solution:

118.4 mM NaCl (mwt 58.44~6.91 g/l)

4.7 mM KCl (mwt 74.56~0.350 g/l)

2.52 mM $CaCl_2$ (mwt 147.02~0.370 g/l)

1.18 mM $MgSO_4$ (mwt 246.5~0.290 g/l)

1.18 mM $KH_2PO_4$ (mwt 136.09~0.160 g/l)

25 mM $NaHCO_3$ (mwt 84.01~2.10 g/l)

pH 7.4

All components are dissolved in 900 ml of deionised water and solution pH is adjusted to 7.4. Adjust volume to 1 liter with deionised water and confirm the pH prior to use. Ringer's solution is mixed 1:1 with Foetal Bovine serum (Gibco ref 16000-036) to produce mock wound fluid.

Example 6—Online EIS Experiments

Electrode Preparation and Measurement Information

For online detection screen printed gold electrodes (Working electrode diameter 1.6 mm) were purchased from DropSens (Oviedo, Spain). Each electrode was pre-cleaned by cyclic voltammetry in 0.1 M $H_2SO_4$. Electrode potential was scanned between 0 and 1.6 V for 20 cycles with care being taken to remove any bubbles forming on the surface with a pipette. A second round of cleaning in 0.1 M $H_2SO_4$ was then carried out where cyclic voltammetry was again performed, this time electrodes were scanned between potentials of 0 and 1.3 V for 20 cycles. Finally, the electrodes were thoroughly rinsed with deionised water and dried under a stream of nitrogen. After cleaning, screen printed electrodes were incubated with a solution of 1.5 µM thiol-modified PNA solution+30 µM mercaptohexanol in 50% (v/v) DMSO for 16 h at room temperature in a humidity chamber. In order to block the surface, electrodes were rinsed in 50% (v/v) DMSO and incubated in 1 mM mercaptohexanol in 50% (v/v) DMSO for 1 h at room temperature in a humidity chamber. Finally, the electrodes were washed with 50% (v/v) DMSO and the EIS measurement buffer (0.1 mM $K_4[Fe(CN)_6]$+0.1 mM $K_3[Fe(CN)_6]$+pH 7.0 10 mM phosphate buffer. Online EIS measurements were performed with a screen printed electrode (WE-Au, CE-Pt, RE-Ag) connected to an Autolab potentiostat. EIS measurements were performed at a DC potential of 0.03 V with an amplitude of 10 mV rms using a frequency range between 100,000 Hz-0.1 Hz (15 frequencies) in 0.1 mM $K_4[Fe(CN)_6]$+0.1 mM $K_3[Fe(CN)_6]$+pH 7.0 10 mM phosphate buffer.

DNA Fragmentation Experiments

The behaviour of the DNA sample following heat pretreatment was analysed. This was done to see if sample fragmentation influenced the EIS result. These experiments were performed on an Agilent 2100 Expert Bioanalyzer (Agilent Technologies; Palo Alto, Calif., USA). Samples of isolated bacterial gDNA were prepared by heating at 95° C. for 0, 1 or 5 mins in a variety of solutions including pure water and 2×SSC. Following treatment 1 µL of sample was loaded into individual wells on a DNA 500 Labchip kit (Agilent Technologies; Palo Alto, Calif., USA). Each chip contained 12 wells and was loaded as required prior to electrophoresis. Upon completion of the automated electrophoresis program the results were analysed using the proprietary software. This enabled the resolution and positioning of individual peaks and also allowed quantification of DNA by integration to find peak area.

Chemical Structures of Spacer Molecules

Spacer molecules were incorporated into the PNA probe in order to improve hybridisation efficiency at the electrode surface. The chemical structures of the AEEA (Probe 01) and AEEEA (Probe 02) ethylene glycol linkers were as follows:

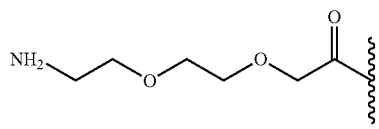

AEEA linker - 1.3 nm & 9 atoms

-continued

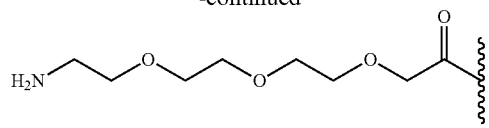

AEEEA linker - 1.8 nm & 12 atoms

Results qPCR and Quantification of gDNA Samples

Samples of genomic DNA were prepared in two ways:

1) gDNA was extracted from a sample of MRSA at $10^8$ cells/mL (1 McFarland standard) spiked into wound fluid. The obtained DNA was then serially 1:10 diluted to give a range of concentrations equivalent to $10^8$ to $10^2$ cells/mL.

2) MRSA was cultivated at $10^8$ cells/mL in wound fluid and then 1:10 serially diluted in wound fluid to give a range of preparations ranging from $10^8$ to $10^2$ cells/mL. The DNA extraction process was performed on each concentration of MRSA.

qPCR was then performed on the samples prepared using the two methods and it was found that the cycle threshold was lower and showed a greater degree of linearity from samples prepared using method 1. This meant that dilution of gDNA extracted from a culture of $10^8$ cells/mL produced more reliable dilution series than by diluting cultures of MRSA and then performing a DNA extraction. results are shown in FIG. 13.

To better understand any variation observed in EIS data, extracts of genomic DNA were quantified using a NanoDrop spectrophotometer (see Table 3). It can be seen that yields of MRSA genomic DNA showed considerable variation along with levels of recovered DNA from human wound fluid alone. The heterogeneous nature of the DNA extraction process is likely to contribute to variation observed in the EIS data. Efforts were made to ensure good reproducibility of data. As shown in FIG. 14 (FIG. 14 shows qPCR data demonstrating variation in gDNA yield upon extraction from $10^8$ cells/mL MRSA in wound fluid) reproducibility was good from a single batch of wound fluid. Batch to batch variation was higher and this can be attributed to the variable nature of human wound fluid and other experimental factors such as aggregation of MRSA and variability inherent in the process of enzymatically digesting the MRSA cell wall with lysotaphin.

TABLE 3

| MRSA total DNA quantification using the NanoDrop | | | | | | | | |
|---|---|---|---|---|---|---|---|---|
| | 1. 06/01 | 2. 06/01 | 3. 06/01 | 4. 06/01 | 1. 18/01 | 2. 18/01 | 3. 18/01 | 4. 18/01 |
| MRSA gDNA Quantification (Nanodrop) [ng/µL] | | | | | | | | |
| $10^8$ | 1164.5 | 434.2 | 350.0 | 1164.5 | 340.8 | 263.3 | 701.4 | 529.0 |
| $10^7$ | 47.5 | 22.1 | 35.1 | 47.5 | 63.1 | 69.5 | 19.0 | 179.7 |
| WF neat | 79.0 | 47.2 | 81.2 | 79.0 | 188.4 | 378.6 | 99.3 | — |
| WF $10^{-1}$ | 6.5 | 4.3 | 71.3 | 6.5 | 16.3 | 16.7 | 26.3 | — |
| MRSA qPCR [Ct] | | | | | | | | |
| $10^8$ | 10.93 | 12.10 | 11.63 | — | 10.7 | 9.7 | 10.09 | 9.96 |
| $10^7$ | 13.23 | 13.81 | 15.26 | — | 12.53 | 13.53 | 13.29 | 13.16 |
| WF neat | — | — | — | — | — | — | — | — |
| WF $10^{-1}$ | — | — | — | — | — | — | — | — |

Prototype Potentiostat for Point of Care Testing

With point of care testing in mind a prototype potentiostat was designed and assembled. The potentiostat was assembled with parts totalling less than US$200 and was able to measure phase and magnitude changes over a frequency range of 100,000 to 0.1 Hz. The system was initially evaluated using a fully complementary short artificial target and it was found that increases in charge transfer resistance following target addition were observable. FIG. 15 shows (A) an image of the prototype potentiostat, and (B) a Nyquist plot pre and 10 minutes post introduction of a 23 bp fully complementary oligonucleotide (1 μM).

DNA Fragmentation

FIGS. 16 A, B & C show bioanalyser data of MRSA gDNA following heat treatment at 95° C. for 0, 1 and 5 mins respectively. It can be seen that heat denaturation time coincided with the production of smaller fragments of DNA. Similar samples were also analysed by gel electrophoresis (FIG. 17) and whilst DNA fragmentation was observed from heat treated fragments sizing was not possible due to smearing of the sample.

Example 7—Further EIS Experiments

Materials and Methods

DNA oligonucleotides were purchased from Metabion (Martinsried, Germany). PNA oligonucleotides were ordered via Cambridge Research Biochemicals (Cleveland, UK) from Panagene (Daejeon, South Korea). PCR kit and DNeasy blood and tissue kit were purchased from Qiagen (Crawley, UK). Potassium ferricyanide, potassium ferrocyanide, sodium saline citrate (SSC), monosodium phosphate, disodium phosphate and dimethyl sulfoxide (DMSO) were purchased from Sigma Aldrich (Poole, UK). Lambda exonuclease (Epicentre Biotechnologies, Madison, Wis., USA) Deionised water was used throughout the study (>18 MΩ).

TABLE 4

Sequences and structures of oligonucleotides used during the study.

| | Oligo name | Type | 3' Modif. | 5' Modif. | Sequence 5'-3' |
|---|---|---|---|---|---|
| 1 | P48 mecA | DNA | — | Thiol-C6 | ACTAGGTGTTGG TGAAGATATACC (SEQ ID NO: 1) |
| 2 | mecA primer 1 | DNA | — | — | AAAATCGATGGT AAAGGTTGGC (SEQ ID NO: 2) |
| 3 | mecA primer 2 | DNA | — | — | AGTTCTGCAGTA CCGGATTTGC (SEQ ID NO: 3) |
| 4 | PNA48 | PNA | — | 0.6 nm Thiol-C6 | ACTAGGTGTTGG TGAAGATATAC (SEQ ID NO: 4) |
| 5 | PNA 48_01 | PNA | — | 1.6 nm-Thiol-C6-AEEA | ACTAGGTGTTGG TGAAGATATAC (SEQ ID NO: 5) |
| 6 | PNA 48_02 | PNA | — | 3.8 nm-Thiol-C11-AEEEA | ACTAGGTGTTGG TGAAGATATAC (SEQ ID NO: 6) |
| 7 | PNA 48_02 | PNA | — | 2 nm-Thiol-(His)$_6$ | ACTAGGTGTTGG TGAAGATATAC (SEQ ID NO: 7) |

DNA Extraction from *S. Aureus*

Bacteria were sub cultured onto Columbia blood agar and incubated overnight at 37° C. in a 5% $CO_2$ atmosphere. Cells were inoculated into saline and the optical density measured using a Densicheck (bioMerieux). This gave values in McFarland units, proportional to the cellular concentration of bacteria in the suspension. A bacterial cell suspension of approximately 10⁸ cells/mL was produced in this way and ten-fold dilutions ranging down to 10² cells/mL prepared from this suspension. Real time PCR was performed to characterise the DNA yields from the dilution series.

The bacterial cells were pelleted by centrifuging 1 mL of the suspension at 5000×g for 10 mins. The supernatant was discarded and the bacterial pellet re-suspended in 200 μL of enzymatic lysis buffer (2×TE buffer, 1.2% Triton X, 50 μg/mL Lysostaphin), before incubating for 30 mins at 37° C. 200 μL of bacterial lysate was added to 20 μL Proteinase K and DNA extracted using the bioMerieux NucliSens easy-MAG automated platform. Guanidine thiocyanate was the active chaotropic agent in the lysis buffer, acting as a protein denaturant in the purification and extraction of nucleic acids from cellular material. The purified nucleic acid solution was then removed from the vessel without dislodging the magnetic silica pellet—DNA was eluted in 100 μL of water.

Electrochemical Impedance Spectroscopy (EIS)

Gold disk electrodes (2 mm diameter) were purchased from IJ Cambria Scientific (Carms, UK). Each solid gold working electrode was thoroughly pre-cleaned by mechanical polishing with 0.05 μm alumina powder (IJ Cambria Scientific (Carms, UK) for 1 min, rinsing with water and immersing in an ultrasonic water bath for 1 min (to eliminate any residual alumina) and finally cleaning for 10 min in piranha solution (6 mL concentrated $H_2SO_4$+2 mL 30% (v/v) $H_2O_2$ solution). Then the electrodes were thoroughly washed with water and dried under a stream of nitrogen. After cleaning, the gold disk electrodes were incubated with a solution of 1.5 μM thiol-modified PNA solution+30 μM mercaptohexanol in 50% (v/v) DMSO for 16 h at 30° C. Electrodes were rinsed in 50% (v/v) DMSO and incubated in 1 mM mercaptohexanol in 50% (v/v) DMSO for 1 h at 30° C. Then the electrodes were washed with 50% (v/v) DMSO and the EIS measurement buffer (0.1 mM $K_3[Fe(CN)_6]$+0.1 mM $K_4[Fe(CN)_6]$+10 mM phosphate buffer) for 2 h and 1 h respectively.

EIS measurements in batch end point assays were performed using a three electrode system with an Ag/AgCl reference electrode and a platinum wire counter electrode (both from Metrohm (Runcorn, UK) connected to an Autolab potentiostat running FRA software (Metrohm, Runcorn, UK). EIS measurements were performed at a DC potential of 0.24 V with an amplitude of 10 mV rms using a frequency range between 100,000 Hz-0.1 Hz (15 frequencies) in 0.1 mM $K_3[Fe(CN)_6]$+0.1 mM $K_4[Fe(CN)_6]$+10 mM phosphate buffer. The DNA sample was prepared by mixing 45 μL of sample with 5 μL of 20×SSC and then heating at 95° C. for 5 mins, storing on ice for 2 mins and heating at 30° C. for 5 mins. The electrode was incubated with the sample for 2 h at 55° C. with shaking (650 rpm). Following incubation with sample, electrodes were washed with 2×SSC, 0.2×SSC and EIS measurement buffer for 10 mins in each. EIS measurements were performed pre and post hybridisation.

The online assay was performed by recording continuous EIS measurements with a screen printed electrode. A single well from a Schott Nexterion 16-well self-adhesive superstructure (Stafford, UK) was cut out and fitted around the electrode in which 50 μL of EIS measurement buffer was present. The well was sealed with an adhesive lid from the Schott Nexterion 16-well self-adhesive superstructure kit (Stafford, UK). 45 µL of sample was mixed with 5 µL of 10×EIS measurement buffer and pre-treated by heating at 95° C. for 5 mins, storing on ice for 2 mins and heating at 30° C. for 5 mins. Once the sample was prepared the EIS measurement buffer was removed from the electrode surface and replaced with the 50 µL sample+measurement buffer solution. The adhesive lid was resealed and EIS measurements continued.

Results and Discussion

In a previous study a probe sequence for the mecA gene was identified and optimised for the impedimetric detection of a 550 base pair mecA PCR product. The probe (P48) was found to be most effective at binding the mecA sequence in a 5' configuration in DNA form on a microarray system and in PNA form for EIS measurements.

Direct Detection of Genomic DNA from MRSA in Batch End Point Assay Format

EIS measurements were carried out pre and post hybridisation and recorded in the form of a Nyquist Plot (see FIG. 18) in order to obtain values for the charge transfer resistance (RCT). Following incubation with MRSA gDNA extracted from a suspension of 107 cells/mL it was found that significant increases in RCT were apparent (see FIG. 18). To obtain values for RCT, data was fitted using a Randles circuit (at the top of the Figure) and the fitting function within the FRA Autolab software. The uncertainty associated with fitting RCT was in the range of 6-12% for the reported experiments. For a particular concentration of gDNA the RCT value obtained post hybridisation was divided by the value obtained pre hybridisation. This approach towards expressing the data provided a measure of the signal increase which corrected for variation in the RCT starting values. Plots showing such data have y-axes denoted as "Signal Increase Ratio". Similar approaches to representing hybridisation induced impedimetric increases have been employed in journal publications. Where used, standard deviation (S.D) is defined as the square root of the variance.

Hybridisation Efficiency—Effect of Incorporating Different Spacers into the Probe Sequence In microarrays and other surface based DNA detection technologies, the kinetics of DNA hybridisation can be improved by enhancing accessibility of the surface probe to species in solution. The hybridisation kinetics are likely to be hindered with the probe sequence in close proximity to the electrode surface and therefore, three probes (01, 02 & 03) with identical sequence to the original (P48) but containing additional spacer schemes were tested for their response after hybridisation with MRSA gDNA at a concentration of 107 cells/mL. The details of the probe spacers are presented in Table 4. The AEEA abbreviation is used to represent a linker containing two ethylene glycol units and the AEEEA abbreviation to represent a linker containing three ethylene glycol units. The chemical structures of the spacer molecules are those already described above.

FIG. 19 shows that of the four probes tested, probe P48_02 showed the greatest signal increase ratio following sample incubation. C11 spacers (spacers with 11 C atoms in their backbone) proved the most effective in this study when attempting to improve DNA binding kinetics at the solid-liquid interface. Enhancement of DNA binding kinetics with the C11 spacer is attributed to the formation of a more densely packed and better ordered mixed film and the likely explanation is thought to be due to increased van der Waals' forces from the C11 spacer. Also the use of a long PEG molecule in combination with C11 spacer allows good flexibility of the probe molecules and ensures the probe sequence protrudes out above the alkanethiol film which coats the electrode surface. For the rest of the study, probe P48_02 was employed as the recognition element on the electrode surface.

Hybridisation Efficiency—Role of DNA Fragmentation in Assay Performance

In these experiments, samples from bacteria cultured at 107 cells/mL were incubated with the electrode for 2 hours prior to washing and measurement. Accompanying gel electrophoresis experiments were performed where the degree of DNA fragmentation during sample denaturation was assessed. This was carried out by heating samples of MRSA gDNA (107 cells/mL) for time periods of 0, 1 and 5 minutes, at temperatures of either 75 or 95° C. in pure water or 2×SSC. It was found that observable fragmentation took place when the sample was heated in 2×SSC for 5 minutes at 95° C. (See FIGS. 20A & 20B). The MRSA genome is approximately 2.8 Mb. The untreated gDNA extracted from MRSA contained large fragments ranging from 1000 to 15000 bp and the fragments observed after heat denaturation for 5 mins were found to be average around 120 bp.

From FIG. 20 it can be seen that denaturation of the genomic DNA for 5 mins at 95° C. in 2×SSC coincided with an increase in DNA fragmentation and an increase in the impedimetric signal. The role of DNA fragmentation has been assessed for glass microarrays with long hybridisation times but has hitherto not been investigated for the binding of genomic DNA for impedimetric detection. It is known that incubation of DNA at a high temperature such at 95° C. causes fragmentation of long strands of DNA and reduces PCR efficiency. Thermal DNA fragmentation has been shown to produce strands of less than 800 bp. The DNA obtained post heat denaturation in this test may be single stranded therefore making it appear shorter when sized post electrophoresis. It is believed that the 95° C. incubation fragmented the high molecular weight MRSA gDNA and this resulted in improved impedance signals. Having obtained an understanding of the roles of spacer choice and DNA fragmentation and with a capillary gel electrophoresis measurement which provided an approximate size for the DNA targets, an assay for MRSA gDNA was devised and evaluated.

Development of a Batch End Point Assay for MRSA gDNA

An MRSA batch end point assay was developed. A DNA denaturation time of 5 minutes was employed in order to achieve fragmentation and non-specific sequences of gDNA from *E. coli* and methicillin susceptible *Staphylococcus aureus* (MSSA) were also tested so that assay specificity could be evaluated. The concentrations of MRSA tested ranged from 103-108 cells/mL.

Figure 21A:
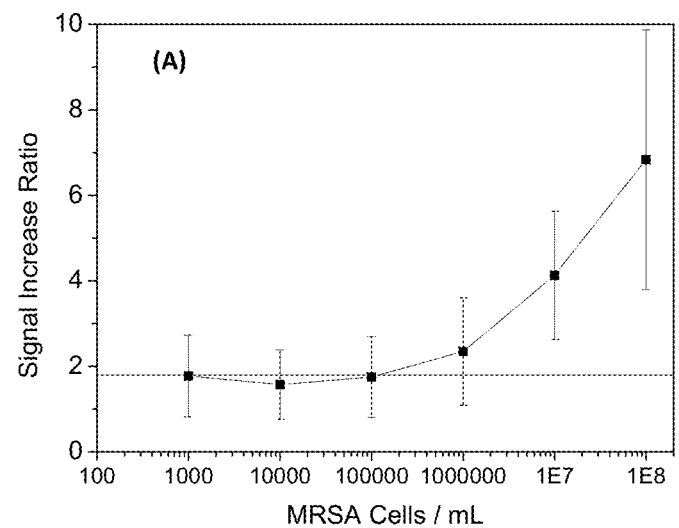

FIG. 21A shows that it was possible to detect MRSA gDNA hybridisation having extracted the DNA from MRSA cells spiked into saline. Using a definition of the signal increases ratio from incubations of 0 MRSA cells/mL plus three standard deviations the L.O.D was 106 cells/mL. The significance of this result lies in the fact that it was possible to detect hybridisation of the mecA gene without performing PCR on the extracted DNA. The maximum concentration of the mecA gene from samples spiked at 106 cells/mL and extracted was ~500 fM.

Figure 21B:
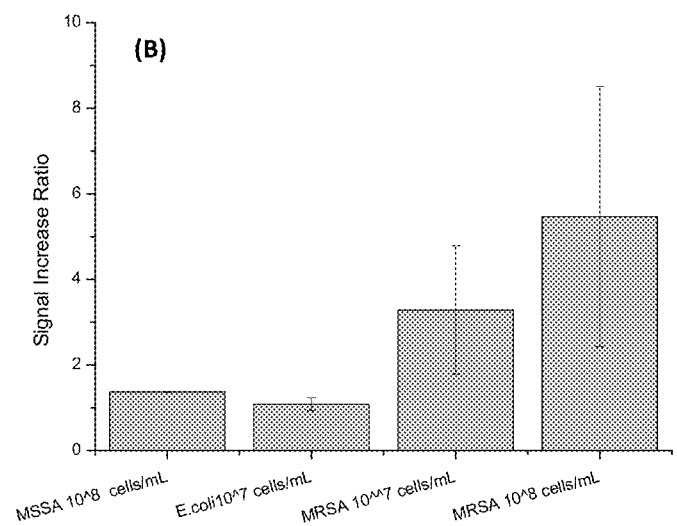

To confirm the specificity of the assay for MRSA gDNA, incubation of probe modified electrodes was carried out in the presence of *E. coli* gDNA and MSSA gDNA at comparable concentrations to the MRSA tests. FIG. 21(B) presents signal increases arising from such incubations and it can be seen that these signal increases were not observed in the presence of *E. coli* and MSSA gDNA. Concentrations of 3-6 pM were equivalent to yields of DNA extracted from bacterial suspensions of 107 cells/mL.

Online MRSA gDNA Detection from Samples Spiked into Human Wound Fluid and Specificity Tests.

The ability to detect binding of gDNA in real time and in the presence of an interfering matrix would amount to a tremendous advantage in terms of a point-of-care test. With this in mind the assay was transferred from gold macrodisk electrodes to screen printed electrodes onto which sample introduction could take place at room temperature and in small volumes. A further advantage of screen printed electrodes is their price (<$3 each) which makes them an attractive component for a point of care test. In these experiments, EIS measurements were performed in a continuous fashion with a full Nyquist plot being produced approximately every two minutes. 100 µL of EIS measurement buffer was incubated on the electrode and after a series of baseline measurements was replaced with 100 µL of previously heat denatured MRSA gDNA (95° C. for 5 mins) or similarly treated human DNA extracted from wound fluid preparations. Charge transfer resistance was plotted versus time and it was possible to measure signal increase ratio at various time points following sample addition (FIG. 22) and thereby obtain binding isotherms associated with the process of DNA hybridisation (FIG. 23).

From FIG. 22 it can be seen that MRSA gDNA spiked into and recovered from human wound fluid caused a much larger increase in the impedimetric signal than DNA samples extracted from a dilution series of human wound fluid. Therefore in this format it was possible to measure MRSA gDNA hybridisation above a background signal caused by extracted human DNA. FIG. 23 shows that when equal amounts of MRSA and $E.$ $coli$ gDNA were added to the sensor, it was possible to discriminate between specific and non-specific binding in this case. The significance of these results lies in the fact that MRSA detection was shown possible in an online test where detection times were much shorter. For example, the data in FIG. 22 show signal increases 10 minutes after sample addition while FIG. 23 shows that a divergence between the binding curves following addition of MRSA and $E.$ $coli$ 107 cells/mL was apparent only approximately 5 minutes after sample addition.

In a wider context these results show that detection of MRSA gDNA was possible without electrode modification through the use of nanostructures or polymeric layers. Additionally, signal enhancement strategies such as gold nanoparticles and protein G have been employed as possible methods for detecting PCR product hybridisation by EIS. The relative simplicity of the electrode preparation process detailed here and the lack of protein or nanoparticle based signal amplification steps are an advantage over many other electrochemical detection schemes.

The data on spacer choice and target fragmentation time show that a relationship between probe length, fragment length and EIS signal exists. The fragmentation data suggests target strand lengths of approximately 120 bp in length are responsible for the EIS signal increases. Much of the literature on EIS based nucleic acid detection reports results obtained with short (~20 bp) artificial oligonucleotides.

The relative simplicity of the current detection scheme (and the fact that a prototype portable potentiostat with good equivalence to a bench top potentiostat and is compatible with screen printed electrodes and which costs less than US $200) has already been produced, means that the assay is well placed for implementation in point-of-care scenarios.

CONCLUSIONS

A sensitive and specific biosensor for the label free detection of MRSA has been demonstrated. The use of a PNA probe sequence allows sensitive detection of MRSA genomic DNA and the assay does not require a PCR amplification step. DNA fragmentation and distance of the probe sequence from the electrode surface are shown to be important factors in assay performance. Fragments were found to be around 120 bp in length, which are longer than the DNA sequences typically reported in EIS studies. Detection of MRSA gDNA was shown to be possible in a batch assay on macro gold electrodes and in an online format on screen printed electrodes. Also it was possible to make detections when DNA was extracted from an interfering matrix such as human wound fluid.

The invention claimed is:

1. A method for detecting an analyte in a sample, wherein the analyte comprises a nucleic acid, which method comprises:
    (a) subjecting the sample to a sample preparation step to fragment the nucleic acid;
    (b) contacting the sample with a peptide nucleic acid (PNA) probe; and
    (c) performing an electrochemical impedance spectrometry (EIS) measurement on the sample comprising:
        (i) applying an alternating voltage to the analyte;
        (ii) determining the rate of change of EIS measurements across the analyte, and
        (iii) determining the presence, absence, quantity and/or identity of the analyte from the rate of change data.

2. A method according to claim 1, wherein no amplification step and/or no concentration step is performed on the sample prior to step (c) and wherein the quantity of analyte in the sample when the sample is taken, is substantially the same as the quantity of analyte in the sample when the sample is subjected to the EIS measurement.

3. A method according to claim 1, wherein the analyte comprises ribosomal RNA and/or genomic DNA.

4. A method according to claim 1, wherein the analyte nucleic acid comprises 1000 bases (1 kb) or more.

5. A method according to claim 1, wherein prior to step (c) no PCR step is performed.

6. A method according to claim 1, wherein prior to step (c) no RTPCR step is performed.

7. A method according to claim 1, wherein the EIS measurements are measurements of electron transfer resistance, Ret.

8. A method according to claim 1, wherein the EIS measurements are measurements calculated from finding the width of the semicircular feature in a Nyquist plot.

9. A method according to claim 1, wherein step (c) comprises a step of performing a Fourier transform on EIS data.

10. A method according to claim 1, wherein an electrolyte is added to the system to aid in EIS measurement.

11. A method according to claim 10, wherein the electrolyte is a transition metal complex.

12. A method according to claim 11, wherein the transition metal complex comprises the $[Fe(CN)_6]^{3-/4-}$ system.

13. A method according to claim 1, wherein a liquid medium is employed in the system to aid in EIS measurement.

14. A method according to claim 13, wherein the liquid medium is acidic or basic.

15. A method according to claim 1, wherein the method is for analysing two or more analytes, and further comprises the step of labelling each analyte with one or more labels to form labelled analytes distinguishable from each other by their labels.

16. A method according to claim 15, wherein the one or more labels are suitable for optical and/or electrical detection.

17. A method according to claim 16, wherein the labels are selected from nanoparticles, single molecules, chemiluminescent enzymes and fluorophores.

18. A method according to claim 17, wherein the labels are nanoparticles comprising a collection of molecules and/or atoms.

19. A method according to claim 18, wherein the nanoparticles are selected from metals, metal nanoshells, metal binary compounds and quantum dots.

20. A method according to claim 16, wherein the optical detection method is selected from optical emission detection, optical absorbance detection, optical scattering detection, spectral shift detection, surface plasmon resonance imaging, and surface-enhanced Raman scattering from adsorbed dyes.

21. A method according to claim 16, wherein the optical detection is optical emission detection and comprises the steps of irradiating the labelled analytes with light capable of exciting the labels and detecting the frequency and intensity of light emissions from the labels.

22. A method according to claim 21, wherein the light is laser light.

23. A method according to claim 21, wherein the light is selected from infra-red light, visible light and UV light.

24. A method according to claim 23, wherein the light is white light.

25. A method according to claim 1, wherein the PNA probe comprises a spacer portion and a PNA portion.

26. A method according to claim 25, wherein the spacer portion comprises two or more groups selected from: a terminal group for attaching the spacer to a surface; an alkyl group; an ether group; and a carbonyl group, and/or wherein the spacer portion comprises 3 or more atoms in its backbone.

27. A method according to claim 25, wherein the spacer portion comprises the following formula:

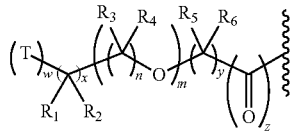

where T is a terminal group capable of attaching to a surface; $R_1$, $R_2$, $R_3$, $R_4$, $R_5$ and $R_6$ are each independently organic groups; w is an integer of 0 or 1; x is an integer of from 0-15; y is an integer of from 0-15; z is an integer of 0 or 1; n is an integer of from 0-10; m is an integer of from 0-15; and wherein [n·m+w+x+y+z] is at least 3.

28. A method according to claim 1, wherein the sample preparation step comprises heating the sample, and/or sonicating the sample.

29. A method according to claim 1, wherein the sample preparation step fragments the nucleic acid in the sample such that the average length of the nucleic acid sequences less than 1000 bp (bp=base pairs), less than 800 bp, less than 500 bp, 20 bp or more, 30 bp or more, 40 bp or more, 50 bp or more 60 bp or more 70 bp or more, 80 bp or more, 90 bp or more, 100 bp or more, 110 bp or more, 120 bp or more, 130 bp or more, 140 bp or more, or 150 bp or more, from 20-800 bp, 30-600 bp, 40-500 bp, 50-400 bp, 60-350 bp, 70-300 bp, 80-250 bp, 90-200 bp, 100-180 bp, or about 120 bp.

30. A method of detecting a pathogen in a wound in a subject, which method comprises detecting a nucleic acid characteristic of the pathogen by performing a method as defined in claim 1.

31. A method according to claim 30, wherein the sample is a sample taken from a wound in the subject.

32. A method according to claim 30, wherein the subject is a human.

33. A method according to claim 30, wherein the pathogen is a pathogen which is resistant to treatment.

34. A method according to claim 30, wherein the pathogen is selected from an *E. coli* and an MRSA.

35. A method for detecting an analyte in a sample, wherein the analyte comprises nucleic acids, the method comprising:
(a) subjecting the sample to a sample preparation step to fragment the nucleic acids;
(b) contacting the sample with a peptide nucleic acid (PNA) probe; and
(c) performing an electrochemic impedance spectrometry (EIS) measurement on the sample, comprising the steps of:
(i) applying an alternating voltage to the analyte, wherein the alternating voltage comprises a plurality of superimposed frequencies sufficient to distinguish the presence of the analyte by electrochemical impedance spectrometry (EIS); and
(ii) determining the presence, absence, identity and/or quantity of the analyte from EIS data.

36. A method according to claim 35, wherein the EIS data comprises data parameters derived from the complex impedance (x+iy), which parameters are selected from one or more of the following:
Real component (x)
Imaginary component (y)
Modulus or absolute value $[r=|z|=(x^2+y^2)^{1/2}]$
Angle $[\theta=\tan-1(y/x)]$.

37. A method according to claim 35, wherein the plurality of frequencies is determined prior to step (b) by statistical analysis, and/or by empirical methods.

38. A method according to claim 35, wherein the minimum number of superimposed frequencies is from 2-20.

39. A method according to claim 38, wherein the number of superimposed frequencies is at least 3-10.

40. A method according to claim 35, wherein the number of superimposed frequencies is at least 7.

* * * * *

SEQUENCE LISTING

```
<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: P48 mecA
<220> FEATURE:
<221> NAME/KEY: misc_feature
<222> LOCATION: (1)..(1)
<223> OTHER INFORMATION: Thiol-C6 modification

<400> SEQUENCE: 1
actaggtgtt ggtgaagata tacc                                          24

<210> SEQ ID NO 2
<211> LENGTH: 22
<212> TYPE: DNA
<213> ORGANISM: Artificial Sequence
<220> FEATURE:
<223> OTHER INFORMATION: mecA primer 1

<400> SEQUENCE: 2
```
aaaatcgatg gtaaaggttg gc                                              22

<210> SEQ ID NO 3
<211> LENGTH: 22
<212> TYPE: DNA
<213> ORGANISM: Artificial Sequence
<220> FEATURE:
<223> OTHER INFORMATION: mecA primer 2

<400> SEQUENCE: 3
agttctgcag taccggattt gc                                              22

<210> SEQ ID NO 4
<211> LENGTH: 23
<212> TYPE: DNA
<213> ORGANISM: Artificial Sequence
<220> FEATURE:
<223> OTHER INFORMATION: PNA48 peptide nucleic acid
<220> FEATURE:
<221> NAME/KEY: misc_feature
<222> LOCATION: (1)..(1)
<223> OTHER INFORMATION: 0.6 nm Thiol-C6 modification

<400> SEQUENCE: 4
actaggtgtt ggtgaagata tac                                             23

<210> SEQ ID NO 5
<211> LENGTH: 23
<212> TYPE: DNA
<213> ORGANISM: Artificial Sequence
<220> FEATURE:
<223> OTHER INFORMATION: PNA 48_01 peptide nucleic acid
<220> FEATURE:
<221> NAME/KEY: MISC_FEATURE
<222> LOCATION: (1)..(1)
<223> OTHER INFORMATION: 1.6 nm - Thiol - C6 - AEEA modification

<400> SEQUENCE: 5
actaggtgtt ggtgaagata tac                                             23

<210> SEQ ID NO 6
<211> LENGTH: 23
<212> TYPE: DNA
<213> ORGANISM: Artificial Sequence
<220> FEATURE:
<223> OTHER INFORMATION: PNA 28_02 peptide nucleic acid
<220> FEATURE:
<221> NAME/KEY: misc_feature
<222> LOCATION: (1)..(1)
<223> OTHER INFORMATION: 3.8 nm - Thiol-C11- AEEEA modification

<400> SEQUENCE: 6
actaggtgtt ggtgaagata tac                                             23

<210> SEQ ID NO 7
<211> LENGTH: 23
<212> TYPE: DNA
<213> ORGANISM: Artificial Sequence
<220> FEATURE:
<223> OTHER INFORMATION: PNA_48_02 peptide nucleic acid
<220> FEATURE:
<221> NAME/KEY: misc_feature
<222> LOCATION: (1)..(1)
<223> OTHER INFORMATION: 2 nm - Thiol- (His)6 modification

<400> SEQUENCE: 7
actaggtgtt ggtgaagata tac                                             23